US011084819B2

(12) United States Patent
Sieger et al.

(10) Patent No.: US 11,084,819 B2
(45) Date of Patent: *Aug. 10, 2021

(54) POLYMORPHS

(71) Applicant: Boehringer Ingelheim International GmbH, Ingelheim am Rhein (DE)

(72) Inventors: Peter Sieger, Mittelbiberach (DE); Dirk Kemmer, Windesheim (DE); Peter Kohlbauer, Biberach an der Riss (DE); Thomas Nicola, Mainz (DE); Martin Renz, Eberhardzell-Dietenwengen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/662,406

(22) Filed: Oct. 24, 2019

(65) Prior Publication Data
US 2020/0055856 A1 Feb. 20, 2020

Related U.S. Application Data

(63) Continuation of application No. 16/373,971, filed on Apr. 3, 2019, now abandoned, which is a continuation of application No. 15/725,426, filed on Oct. 5, 2017, now Pat. No. 10,301,313, which is a continuation of application No. 15/285,871, filed on Oct. 5, 2016, now Pat. No. 9,815,837, which is a continuation of application No. 14/994,578, filed on Jan. 13, 2016, now Pat. No. 9,493,462, which is a continuation of application No. 14/462,654, filed on Aug. 19, 2014, now Pat. No. 9,266,888, which is a continuation of application No. 13/563,767, filed on Aug. 1, 2012, now abandoned, which is a continuation of application No. 11/744,700, filed on May 4, 2007, now abandoned.

(30) Foreign Application Priority Data

May 4, 2006 (EP) ..................................... 06009202

(51) Int. Cl.
C07D 473/04 (2006.01)
C07D 473/06 (2006.01)

(52) U.S. Cl.
CPC ......... *C07D 473/06* (2013.01); *C07D 473/04* (2013.01); *C07B 2200/13* (2013.01)

(58) Field of Classification Search
CPC .................................................. C07D 473/04
See application file for complete search history.

(56) References Cited

U.S. PATENT DOCUMENTS

| | | |
|---|---|---|
| 2,056,046 A | 9/1936 | Fourneau |
| 2,375,138 A | 5/1945 | Victors |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,159,345 A | 6/1979 | Takeo et al. |
| 4,382,091 A | 5/1983 | Benjamin et al. |
| 4,599,338 A | 7/1986 | Regnier et al. |
| 4,639,436 A | 1/1987 | Junge et al. |
| 4,687,777 A | 8/1987 | Meguro et al. |
| 4,743,450 A | 5/1988 | Harris et al. |
| 4,764,466 A | 8/1988 | Suyama et al. |
| 4,816,455 A | 3/1989 | Schickaneder et al. |
| 4,873,330 A | 10/1989 | Lindholm |
| 4,968,672 A | 11/1990 | Jacobson et al. |
| 5,034,225 A | 7/1991 | Bennett et al. |
| 5,041,448 A | 8/1991 | Janssens et al. |
| 5,051,509 A | 9/1991 | Nagano et al. |
| 5,051,517 A | 9/1991 | Findeisen et al. |
| 5,084,460 A | 1/1992 | Munson, Jr. et al. |
| 5,120,712 A | 6/1992 | Habener |
| 5,130,244 A | 7/1992 | Nishimaki et al. |
| 5,164,526 A | 11/1992 | Macher |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |

(Continued)

FOREIGN PATENT DOCUMENTS

AU 2003280680 A1 6/2004
AU 2009224546 A1 9/2009

(Continued)

OTHER PUBLICATIONS

Cygankiewicz, Andrzej et al., Investigations into the Piperazine Derivatives of Dimethylxanthine:, Acta Polon Pharm. [Papers of Polish Pharmacology], XXXOV, No. 5, pp. 607-612, 1977.
Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.
Dave, Rutesh H. "Overview of pharmaceutical excipients used in tablets and capsules." Drug Topics, Oct. 24, 2008.
Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.
Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

(Continued)

*Primary Examiner* — John S Kenyon
(74) *Attorney, Agent, or Firm* — David L. Kershner

(57) ABSTRACT

The invention relates to polymorphous crystal modifications of a DPP-IV inhibitor, the preparation thereof and the use thereof for preparing a medicament.

35 Claims, 6 Drawing Sheets

(56) References Cited

U.S. PATENT DOCUMENTS

| | | |
|---|---|---|
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,461,066 A | 10/1995 | Gericke et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,830,908 A | 11/1998 | Grunenberg et al. |
| 5,879,708 A | 3/1999 | Makino et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |
| 6,200,958 B1 | 3/2001 | Odaka et al. |
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,399,101 B1 | 6/2002 | Frontanes et al. |
| 6,448,323 B1 | 9/2002 | Jordan et al. |
| 6,548,481 B1 | 4/2003 | Demuth et al. |
| 6,579,868 B1 | 6/2003 | Asano et al. |
| 6,689,353 B1 | 2/2004 | Wang et al. |
| 6,699,845 B2 | 3/2004 | Asahi |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,890,898 B2 | 5/2005 | Bachovchin et al. |
| 6,995,183 B2 | 2/2006 | Hamann et al. |
| 7,034,039 B2 | 4/2006 | Oi et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,220,750 B2 | 5/2007 | Himmelsbach et al. |
| 7,235,538 B2 | 6/2007 | Kanstrup et al. |
| 7,247,478 B2 | 7/2007 | Eberhardt et al. |
| 7,282,219 B2 | 10/2007 | Nomura et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,754,481 B2 | 7/2010 | Eberhardt et al. |
| 7,799,782 B2 | 9/2010 | Munson et al. |
| 7,820,815 B2 | 10/2010 | Pfrengle et al. |
| 7,838,529 B2 | 11/2010 | Himmelsbach et al. |
| 7,919,572 B2 | 4/2011 | Angot et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 8,338,450 B2 | 12/2012 | Arora et al. |
| 8,399,414 B2 | 3/2013 | Harada et al. |
| 8,455,435 B2 | 6/2013 | Franz et al. |
| 8,513,264 B2 | 8/2013 | Mark et al. |
| 8,541,450 B2 | 9/2013 | Pfrengle et al. |
| 8,637,530 B2 | 1/2014 | Pfrengle et al. |
| 8,664,232 B2 | 3/2014 | Himmelsbach et al. |
| 8,673,927 B2 | 3/2014 | Dugi et al. |
| 8,679,520 B2 | 3/2014 | Horres et al. |
| 8,697,868 B2 | 4/2014 | Himmelsbach et al. |
| 8,785,455 B2 | 7/2014 | Hotter et al. |
| 8,846,695 B2 | 9/2014 | Dugi |
| 8,853,156 B2 | 10/2014 | Dugi et al. |
| 8,865,729 B2 | 10/2014 | Sieger et al. |
| 8,883,800 B2 | 11/2014 | Pfrengle et al. |
| 8,883,805 B2 | 11/2014 | Pfrengle et al. |
| 8,962,636 B2 | 2/2015 | Pfrengle et al. |
| 9,034,883 B2 | 5/2015 | Klein et al. |
| 9,108,964 B2 | 8/2015 | Himmelsbach et al. |
| 9,149,478 B2 | 10/2015 | Klein et al. |
| 9,155,705 B2 | 10/2015 | Friedl et al. |
| 9,173,859 B2 | 11/2015 | Dugi et al. |
| 9,186,392 B2 | 11/2015 | Klein et al. |
| 9,199,998 B2 | 12/2015 | Pfrengle et al. |
| 9,212,183 B2 | 12/2015 | Sieger et al. |
| 9,266,888 B2 * | 2/2016 | Sieger ............... A61P 3/00 |
| 9,321,791 B2 | 4/2016 | Himmelsbach et al. |
| 9,415,016 B2 | 8/2016 | Friedl et al. |
| 9,486,426 B2 | 8/2016 | Eller |
| 9,457,029 B2 | 10/2016 | Dugi et al. |
| 9,486,526 B2 | 11/2016 | Dugi |
| 9,493,462 B2 * | 11/2016 | Sieger ............... A61P 19/02 |
| 9,815,837 B2 * | 11/2017 | Sieger ............... A61P 29/00 |
| 10,023,574 B2 | 7/2018 | Himmelsbach |
| 10,034,877 B2 | 7/2018 | Dugi |
| 10,155,000 B2 | 12/2018 | Meinicke et al. |
| 10,301,313 B2 * | 5/2019 | Sieger ............... A61P 3/04 |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0042393 A1 | 4/2002 | Oobae et al. |
| 2002/0115718 A1 | 8/2002 | Chen et al. |
| 2002/0137903 A1 | 9/2002 | Ellsworth et al. |
| 2002/0160047 A1 | 10/2002 | Hussain et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0040490 A1 | 2/2003 | Sugiyama et al. |
| 2003/0078269 A1 | 4/2003 | Pearson et al. |
| 2003/0100563 A1 | 5/2003 | Edmondson et al. |
| 2003/0104053 A1 | 6/2003 | Gusler et al. |
| 2003/0104983 A1 | 6/2003 | DeFelippis et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |
| 2003/0153509 A1 | 8/2003 | Bachovchin et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0018468 A1 | 1/2004 | Gorokhovsky |
| 2004/0023981 A1 | 2/2004 | Ren et al. |

(56) References Cited

U.S. PATENT DOCUMENTS

| | | |
|---|---|---|
| 2004/0034014 A1 | 2/2004 | Kanstrup et al. |
| 2004/0037883 A1 | 2/2004 | Zhou et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0152659 A1 | 8/2004 | Matsuoka et al. |
| 2004/0152720 A1 | 8/2004 | Hartig et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259903 A1 | 12/2004 | Boehringer et al. |
| 2004/0266806 A1 | 12/2004 | Sanghvi et al. |
| 2005/0020484 A1 | 1/2005 | Harada et al. |
| 2005/0020574 A1 | 1/2005 | Hauel et al. |
| 2005/0026921 A1 | 2/2005 | Eckhardt et al. |
| 2005/0027012 A1 | 2/2005 | Kohlrausch |
| 2005/0031682 A1 | 2/2005 | Cucala Escoi et al. |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0070694 A1 | 3/2005 | Gelfanova et al. |
| 2005/0097798 A1 | 5/2005 | Evans et al. |
| 2005/0107730 A1 | 5/2005 | Doty et al. |
| 2005/0119162 A1 | 6/2005 | Harada et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0244502 A1 | 11/2005 | Mathias et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0008829 A1 | 1/2006 | Hess |
| 2006/0034922 A1 | 2/2006 | Cheng et al. |
| 2006/0039968 A1 | 2/2006 | Manikandan et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Iyer et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0027168 A1 | 2/2007 | Pfrengle et al. |
| 2007/0059797 A1 | 3/2007 | Low et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0173452 A1 | 7/2007 | DiMarchi et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0197552 A1 | 8/2007 | Carr |
| 2007/0219178 A1 | 9/2007 | Muramoto |
| 2007/0254944 A1 | 11/2007 | Hughes |
| 2007/0259880 A1 | 11/2007 | Sakashita et al. |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0265349 A1 | 11/2007 | Rapin et al. |
| 2007/0281940 A1 | 12/2007 | Dugi et al. |
| 2007/0299076 A1 | 12/2007 | Piotrowski et al. |
| 2008/0014270 A1 | 1/2008 | Harada |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0221200 A1 | 9/2008 | Allison et al. |
| 2008/0234291 A1 | 9/2008 | Francois et al. |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0054303 A1 | 2/2009 | Gougoutas et al. |
| 2009/0082256 A1 | 3/2009 | Abe et al. |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0253752 A1 | 10/2009 | Burkey et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0179191 A1 | 7/2010 | Himmelsbach et al. |
| 2010/0183531 A1 | 7/2010 | Johncock et al. |
| 2010/0204250 A1 | 8/2010 | Himmelsbach et al. |
| 2010/0209506 A1 | 8/2010 | Eisenreich |
| 2010/0310664 A1 | 12/2010 | Watson et al. |
| 2010/0317575 A1 | 12/2010 | Pinnetti et al. |
| 2010/0330177 A1 | 12/2010 | Pourkavoos |
| 2011/0009391 A1 | 1/2011 | Braun et al. |
| 2011/0028391 A1 | 2/2011 | Holst et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0212982 A1 | 9/2011 | Christopher et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |

(56) References Cited

U.S. PATENT DOCUMENTS

| | | |
|---|---|---|
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0232004 A1 | 9/2012 | Bachovchin et al. |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0064887 A1 | 3/2013 | Ito et al. |
| 2013/0122089 A1 | 5/2013 | Kohlrausch et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |
| 2013/0236543 A1 | 9/2013 | Ito et al. |
| 2013/0303554 A1 | 11/2013 | Klein et al. |
| 2013/0310398 A1 | 11/2013 | Mark et al. |
| 2013/0315975 A1 | 11/2013 | Klein et al. |
| 2013/0317046 A1 | 11/2013 | Johansen |
| 2013/0324463 A1 | 12/2013 | Klein et al. |
| 2014/0100236 A1 | 4/2014 | Busl et al. |
| 2014/0274889 A1 | 9/2014 | Johansen et al. |
| 2014/0315832 A1 | 10/2014 | Broedl et al. |
| 2014/0343014 A1 | 11/2014 | Klein et al. |
| 2014/0371243 A1 | 12/2014 | Klein et al. |
| 2015/0196565 A1 | 7/2015 | Klein et al. |
| 2015/0246045 A1 | 9/2015 | Klein et al. |
| 2015/0265538 A1 | 9/2015 | Balthes et al. |
| 2016/0058769 A1 | 3/2016 | Graefe-Mody et al. |
| 2016/0082011 A1 | 3/2016 | Klein et al. |
| 2016/0106677 A1 | 4/2016 | Boeck et al. |
| 2016/0310435 A1 | 10/2016 | Friedl et al. |
| 2017/0020868 A1 | 1/2017 | Dugi et al. |
| 2017/0354660 A1 | 12/2017 | Meinicke et al. |

FOREIGN PATENT DOCUMENTS

| | | |
|---|---|---|
| CA | 1123437 A1 | 5/1982 |
| CA | 2136288 A1 | 5/1995 |
| CA | 2375779 | 5/2000 |
| CA | 2418656 A1 | 2/2002 |
| CA | 2435730 A1 | 9/2002 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2558446 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2599419 A1 | 11/2006 |
| CA | 2651019 A1 | 11/2007 |
| CA | 2651089 A1 | 11/2007 |
| CA | 2720450 A1 | 10/2009 |
| CN | 101035522 A | 9/2007 |
| CN | 101234105 A | 8/2008 |
| CN | 101309689 A | 11/2008 |
| CN | 101590007 A | 12/2009 |
| CN | 104130258 A | 11/2014 |
| DE | 2205815 A1 | 8/1973 |
| DE | 2758025 A1 | 7/1979 |
| DE | 19705233 A1 | 8/1998 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EA | 201300121 | 10/2009 |
| EP | 0023032 A1 | 1/1981 |
| EP | 0149578 A2 | 7/1985 |
| EP | 0189941 A2 | 8/1986 |
| EP | 0223403 A2 | 5/1987 |
| EP | 0237608 A1 | 9/1987 |
| EP | 0248634 A2 | 12/1987 |
| EP | 0342675 A2 | 11/1989 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |
| EP | 0524482 A1 | 1/1993 |
| EP | 0638567 A1 | 2/1995 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1310245 A1 | 5/2003 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1523994 A1 | 4/2005 |
| EP | 1535906 A1 | 6/2005 |
| EP | 1537880 A1 | 6/2005 |
| EP | 1557165 A1 | 7/2005 |
| EP | 1586571 A1 | 10/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 1897892 A2 | 3/2008 |
| EP | 2143443 A1 | 1/2010 |
| EP | 2166007 A1 | 3/2010 |
| EP | 2308878 A2 | 4/2011 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 61030567 | 2/1986 |
| JP | 770120 | 3/1995 |
| JP | 8333339 | 12/1996 |
| JP | 11193270 | 7/1999 |
| JP | 2000502684 A | 3/2000 |
| JP | 2001213770 A | 8/2001 |
| JP | 2001278812 A | 10/2001 |
| JP | 2001292388 A | 10/2001 |
| JP | 2002348279 A | 12/2002 |
| JP | 2003286287 A | 10/2003 |
| JP | 2003300977 A | 10/2003 |
| JP | 2004161749 A | 6/2004 |
| JP | 2004196824 A | 7/2004 |
| JP | 2004250336 A | 9/2004 |
| JP | 2005511636 A | 4/2005 |
| JP | 2005519059 A | 6/2005 |
| JP | 2006503013 A | 1/2006 |
| JP | 2006045156 A | 2/2006 |
| JP | 2006137678 A | 6/2006 |
| JP | 2007501231 A | 1/2007 |
| JP | 2007510059 A | 4/2007 |
| JP | 2007522251 A | 8/2007 |
| JP | 2007531780 A | 11/2007 |
| JP | 2008513390 A | 5/2008 |
| JP | 2008536881 A | 9/2008 |
| JP | 2010500326 A | 1/2010 |
| JP | 2010053576 A | 3/2010 |

(56) References Cited

FOREIGN PATENT DOCUMENTS

| | | |
|---|---|---|
| JP | 2010070576 A | 4/2010 |
| JP | 2010524580 A | 7/2010 |
| JP | 2010535850 A | 11/2010 |
| JP | 2010536734 A | 12/2010 |
| JP | 2011088838 A | 5/2011 |
| JP | 2011529945 A | 12/2011 |
| JP | 2012502081 A | 1/2012 |
| JP | 2012505859 A | 3/2012 |
| KR | 20070111099 A | 11/2007 |
| WO | 8706941 A1 | 11/1987 |
| WO | 199107945 A1 | 6/1991 |
| WO | 199205175 A1 | 4/1992 |
| WO | 199219227 A2 | 11/1992 |
| WO | 199402150 A1 | 2/1994 |
| WO | 199403456 A1 | 2/1994 |
| WO | 1994012200 | 6/1994 |
| WO | 9532178 A1 | 11/1995 |
| WO | 199609045 A1 | 3/1996 |
| WO | 199611917 A1 | 4/1996 |
| WO | 199636638 A1 | 11/1996 |
| WO | 199718814 A1 | 5/1997 |
| WO | 199723447 A1 | 7/1997 |
| WO | 199723473 A1 | 7/1997 |
| WO | 199728808 A1 | 8/1997 |
| WO | 199746526 A1 | 12/1997 |
| WO | 1998007725 | 2/1998 |
| WO | 199811893 | 3/1998 |
| WO | 9818770 A1 | 5/1998 |
| WO | 199822464 A1 | 5/1998 |
| WO | 199828007 A1 | 7/1998 |
| WO | 199840069 A2 | 9/1998 |
| WO | 1998046082 A1 | 10/1998 |
| WO | 199856406 A1 | 12/1998 |
| WO | 199929695 A1 | 6/1999 |
| WO | 1999038501 A2 | 8/1999 |
| WO | 199950248 A1 | 10/1999 |
| WO | 1999049857 | 10/1999 |
| WO | 199956561 A1 | 11/1999 |
| WO | 199967279 A1 | 12/1999 |
| WO | 2000003735 A1 | 1/2000 |
| WO | 200012064 A1 | 3/2000 |
| WO | 200072873 | 5/2000 |
| WO | 200034241 A1 | 6/2000 |
| WO | 0069464 A1 | 11/2000 |
| WO | 0072799 A2 | 12/2000 |
| WO | 0078735 A1 | 12/2000 |
| WO | 200072973 A1 | 12/2000 |
| WO | 200073307 A2 | 12/2000 |
| WO | 200107441 A1 | 2/2001 |
| WO | 2001032158 A2 | 5/2001 |
| WO | 2001040180 A2 | 6/2001 |
| WO | 200152825 | 7/2001 |
| WO | 200152852 A1 | 7/2001 |
| WO | 2001047514 A1 | 7/2001 |
| WO | 2001051919 | 7/2001 |
| WO | 2001066548 A1 | 9/2001 |
| WO | 2001068603 | 9/2001 |
| WO | 2001068646 A1 | 9/2001 |
| WO | 200177110 A1 | 10/2001 |
| WO | 2001072290 A2 | 10/2001 |
| WO | 200196301 A1 | 12/2001 |
| WO | 200197808 A1 | 12/2001 |
| WO | 200202560 A2 | 1/2002 |
| WO | 200214271 A1 | 2/2002 |
| WO | 200224698 A1 | 3/2002 |
| WO | 2002053516 A2 | 7/2002 |
| WO | 2002068420 A1 | 9/2002 |
| WO | 2003000241 A2 | 1/2003 |
| WO | 2003000250 | 1/2003 |
| WO | 2003002531 A2 | 1/2003 |
| WO | 2003002553 A2 | 1/2003 |
| WO | 2003004496 A1 | 1/2003 |
| WO | 2003006425 A2 | 1/2003 |
| WO | 2003024965 A2 | 3/2003 |
| WO | 2003033686 A2 | 4/2003 |
| WO | 2003034944 A1 | 5/2003 |
| WO | 2003035177 A2 | 5/2003 |
| WO | 2003037327 A1 | 5/2003 |
| WO | 2003053929 A1 | 7/2003 |
| WO | 2003055881 A1 | 7/2003 |
| WO | 2003057200 A2 | 7/2003 |
| WO | 2003057245 A1 | 7/2003 |
| WO | 2003059327 | 7/2003 |
| WO | 2003061688 A1 | 7/2003 |
| WO | 2003064454 A1 | 8/2003 |
| WO | 2003074500 A2 | 9/2003 |
| WO | 2003088900 A2 | 10/2003 |
| WO | 2003094909 A2 | 11/2003 |
| WO | 2003099279 A1 | 12/2003 |
| WO | 2003099836 A1 | 12/2003 |
| WO | 2003104229 A1 | 12/2003 |
| WO | 2003106428 A1 | 12/2003 |
| WO | 2004002924 A1 | 1/2004 |
| WO | 2004011416 A1 | 2/2004 |
| WO | 2004016587 A1 | 2/2004 |
| WO | 2000003735 | 3/2004 |
| WO | 2004018467 A2 | 3/2004 |
| WO | 2004018468 A2 | 3/2004 |
| WO | 2004018469 A1 | 3/2004 |
| WO | WO-2004018468 A2 * | 3/2004 ........... A61K 9/2866 |
| WO | 2004028524 A1 | 4/2004 |
| WO | 2004033455 A1 | 4/2004 |
| WO | 2004035575 A1 | 4/2004 |
| WO | 2004037169 A2 | 5/2004 |
| WO | 2004041820 A1 | 5/2004 |
| WO | 2004043940 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A1 | 8/2004 |
| WO | 2004074246 A2 | 9/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007137 A2 | 1/2005 |
| WO | 2005007647 A1 | 1/2005 |
| WO | 2005007658 A2 | 1/2005 |
| WO | 2005012288 A1 | 2/2005 |
| WO | 2005016365 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005075410 A1 | 8/2005 |
| WO | 2005082906 A1 | 9/2005 |
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A1 | 10/2005 |
| WO | 2005107730 A2 | 11/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2006005613 A1 | 1/2006 |
| WO | 2006027204 A1 | 3/2006 |
| WO | 2006029577 A1 | 3/2006 |
| WO | 2006029769 A1 | 3/2006 |
| WO | 2006036664 A1 | 4/2006 |
| WO | 2006040625 A1 | 4/2006 |
| WO | 2006041976 A1 | 4/2006 |

(56) References Cited

FOREIGN PATENT DOCUMENTS

| | | |
|---|---|---|
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006078593 A2 | 7/2006 |
| WO | 2006083491 A2 | 8/2006 |
| WO | 2006116157 | 11/2006 |
| WO | 2006129785 A1 | 12/2006 |
| WO | 2006135693 A2 | 12/2006 |
| WO | 2006137085 A1 | 12/2006 |
| WO | 2007007173 A2 | 1/2007 |
| WO | 2007014886 A1 | 2/2007 |
| WO | 2007014895 A2 | 2/2007 |
| WO | 2007017423 A1 | 2/2007 |
| WO | 07035665 A1 | 3/2007 |
| WO | 2007033350 A1 | 3/2007 |
| WO | 2007035355 A2 | 3/2007 |
| WO | 2007035665 A1 | 3/2007 |
| WO | 2007038979 A1 | 4/2007 |
| WO | 2007041053 A2 | 4/2007 |
| WO | 2007050485 A2 | 5/2007 |
| WO | 2007071738 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007136151 A1 | 11/2007 |
| WO | 2007137107 A2 | 11/2007 |
| WO | 2007147185 A1 | 12/2007 |
| WO | 2007148185 A2 | 12/2007 |
| WO | 2007149797 A2 | 12/2007 |
| WO | 2003057245 | 1/2008 |
| WO | 2008005569 A2 | 1/2008 |
| WO | 2008005576 A1 | 1/2008 |
| WO | 2008017670 | 2/2008 |
| WO | 2008017670 A1 | 2/2008 |
| WO | 2008022267 A2 | 2/2008 |
| WO | 2008055870 A1 | 5/2008 |
| WO | 2008055940 A2 | 5/2008 |
| WO | 2008070692 A2 | 6/2008 |
| WO | 2008077639 A1 | 7/2008 |
| WO | 2008081205 A1 | 7/2008 |
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008097180 A1 | 8/2008 |
| WO | 2008113000 A1 | 9/2008 |
| WO | 2008130998 A2 | 10/2008 |
| WO | 2008131149 A2 | 10/2008 |
| WO | 2008137435 A1 | 11/2008 |
| WO | 2009011451 A | 1/2009 |
| WO | 2009022007 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009063072 A2 | 5/2009 |
| WO | 2009091082 A1 | 7/2009 |
| WO | 2009099734 A1 | 8/2009 |
| WO | 2009111200 A1 | 9/2009 |
| WO | 2009112691 A2 | 9/2009 |
| WO | 2009121945 A2 | 10/2009 |
| WO | 2009123992 A1 | 10/2009 |
| WO | 2009147125 A1 | 12/2009 |
| WO | 201092124 | 2/2010 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092125 A1 | 8/2010 |
| WO | 2010092163 A2 | 8/2010 |
| WO | 2010096384 A2 | 8/2010 |
| WO | 2010106457 A2 | 9/2010 |
| WO | 2010126908 A1 | 11/2010 |
| WO | 2010140111 A1 | 12/2010 |
| WO | 2010147768 A1 | 12/2010 |
| WO | 2011011541 A1 | 1/2011 |
| WO | 2011039337 A1 | 4/2011 |
| WO | 2011039367 A2 | 4/2011 |
| WO | 2011064352 A1 | 6/2011 |
| WO | 2011109333 | 9/2011 |
| WO | 2011113947 A1 | 9/2011 |
| WO | 2011138380 A1 | 11/2011 |
| WO | 2011138421 A1 | 11/2011 |
| WO | 2011154496 A1 | 12/2011 |
| WO | 2011161161 A1 | 12/2011 |
| WO | 2011163206 A2 | 12/2011 |
| WO | 2012031124 A2 | 3/2012 |
| WO | 2012039420 A1 | 3/2012 |
| WO | 2012065993 A1 | 5/2012 |
| WO | 2012088682 A1 | 7/2012 |
| WO | 2012089127 A1 | 7/2012 |
| WO | 2012106303 A1 | 8/2012 |
| WO | 2012120040 A1 | 9/2012 |
| WO | 2003061688 | 4/2013 |
| WO | 2013098372 A1 | 7/2013 |
| WO | 2013103629 A1 | 7/2013 |
| WO | 2013131967 A1 | 9/2013 |
| WO | 2013171167 A1 | 11/2013 |
| WO | 2013174768 A1 | 11/2013 |
| WO | 2013179307 A2 | 12/2013 |
| WO | 2014029848 A1 | 2/2014 |
| WO | 2014140284 A1 | 9/2014 |
| WO | 2014170383 A1 | 10/2014 |

OTHER PUBLICATIONS

Deacon, C.F., et al. Inhibitors of dipeptidyl peptidase IV: a novel approach for the prevention and treatment of Type 2 diabetes? Expert Opinion on Investigational Drugs, Sep. 2004, vol. 13, No. 9, p. 1091-1102.

Deacon, Carolyn F., "Dipeptidyl peptidase 4 inhibition with sitagliptin: a new therapy for Type 2 diabetes." Expert Opinion on Investigational Drugs, 2007, vol. 16, No. 4, pp. 533-545.

Definition of "prevent", e-dictionary, Aug. 15, 2013, http://dictionary.reference.com/browse/prevent.

DeMeester, I. et al; "CD26, let it cut or cut it down", Review: Immunology Today; Aug. 1999, vol. 20, No. 8 pp. 367-375.

Demuth, H-U. et al., "Type 2 diabetes—Therapy with dipeptidyl peptidase IV inhibitors". Biochimica et Biophysica Acta, vol. 1751(1), 2005, p. 33-44.

Diabetes Frontier, 2007, vol. 18, No. 2, p. 145-148.

Diabetes Health Center, "Diabetic Retinopathy—Prevention." Retrieved online Mar. 22, 2011. www.diabetes.webmd.com/tc/diabetic-retinopathy-prevention <http://www.diabetes.webmd.com/td/diabetic-retinopathy-prevention?print=true>.

Diabetesincontrol.com "EASD: Eucreas, a Combination of Galvus and Metformin, Recommended for Approval." Diabetes in Control.com, Sep. 25, 2007, Retrieved from internet on Nov. 30, 2012, http://www.diabetesincontrol.com/articles/53-diabetes-news/5145.

Diabetic Neuropathy, Retrieved online Mar. 6, 2012. www.mayoclinic.com/health/diabetic-neuropathy/DS01045/METHOD=print&DSE <http://www.mayoclinic.com/health/diabetic-neuropathy/DS01045/METHOD=print&DSE>.

Dittberner, S. et al., "Determination of the absolute bioavailability of BI 1356, a substance with non-linear pharmacokinetics, using a population pharmacokinetic modeling approach." Abstracts of the Annual Meeting of the Population Approach Group in Europe, 2007.

(56) References Cited

OTHER PUBLICATIONS

Drucker, Daniel J., "Dipeptidyl Peptidase-4 Inhibition and the Treatment of Type 2 Diabetes." Diabetes Care, 2007, vol. 30, No. 6, pp. 1335-1343.

Drucker, et al.., The incretin system:glucagon-like peptide-1 receptor agonists and dipeptidyl peptidase-4 inhibitors in type 2 diabetes. Lancet, 2006, 368: 1696-705.

Dugi, K. et al., "Safety, tolerability, pharmacokinetics, and pharmacodynamics of BI 1356, a novel DPP-IV inhibitor with a wide therapeutic window." Diabetic Medicine, 2006, vol. 23, Suppl. 4, p. 300.

Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.

Dunitz, J. et al., "Disappearing Polymorphs." Acc. Chem. Res. 1995, vol. 28, No. 4, pp. 193-200.

Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.

Edosada, C. Y. et al., "Selective Inhibition of Fibroblast Activation Protein Protease Based on Dipeptide Substrate Specificity." The Journal of Biological Chemistry, 2006, vol. 281, No. 11, pp. 7437-7444.

Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.

EMEA Guidelines on Eucreas®, 2007, pp. 1-27.

EMEA Guidelines on Galvus®, 2007, pp. 1-34.

EMEA: European Medicines Agency, "Galvus (vildagliptin)" Retrieved online on Jan. 21, 2016.

EMEA: European Medicines Agency, ICH Topic E4, "Dose Response Information to Support Drug Registration." 1994, pp. 1-10.

EU Clinical Trial Register, "A multicenter, international, rendomized, parallel group, double-blind, placebo-controlled, cardiovascular safety and renal microvascular outcome study with linagliptin, 5 mg once daily in patients with type 2 diabetes mellitus at high vascular risk." Aug. 19, 2015.

Eucreas Scientific Discussion, 2007, p. 1-27, www.emea.europa.eu/humandocs/PD/Fs/EPAR/eucreas/H-807-en6.pdf, Anonymous.

European Search Report for EP 08 15 9141 dated Apr. 6, 2009 (European counterpart of U.S. Appl. No. 12/143,128).

Eyjolfsson, Reynir "Lisinopril-Lactose Incompatibility." Drug Development and Industrial Pharmacy, 1998, vol. 24, No. 8, pp. 797-798.

Fantus, George, "Metformin's contraindications: needed for now." Canadian Medical Association Journal, 2005, vol. 173, No. 5, pp. 505-507.

Feng, J. et al., "Discovery of Alogliptin: A Potent, Selective, Bioavailable, and Efficacious Inhibitor of Dipeptidyl Peptidase IV." Journal of Medicinal Chemistry, 2007, vol. 50, No. 10, pp. 2297-2300.

Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.

Ferry, Robert Jr., "Diabetes Causes." eMedicine Health, MedicineNet.com, 2013, Retrieved from internet on Aug. 22, 2013,<http://www.onhealth.com/diabetes_health/page3.htm#diabetes_causes>.

Flatt, P.R. et al., "Dipeptidyl peptidase IV (DPP IV) and related molecules in type 2 diabetes." Frontiers in Bioscience, 2008, vol. 13, pp. 3648-3660.

Florez, J. et al. "TCF7L2 Polymorphisms and Progression to Diabetes in the Diabetes Prevention Program." The New England Journal of Medicine, 2006, vol. 355, No. 3, pp. 241-250.

Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.

Forst, T. et al., "The oral DPP-4 inhibitor linagliptin significantly lowers HbA1c after 4 weeks of treatment in patients with type 2 diabetes mellitus." Diabetes, Obesity and Metabolism, 2011, vol. 13, pp. 542-550.

Fukushima et al., Drug for Treating Type II Diabetes (6), "action-mechanism of DPP-IV inhibitor and the availability thereof" Mebio, 2009, vol. 26, No. 8, p. 50-58.

Gall, "Prevalence of micro-and macroalbuminuria, arterial hypertension, retinopathy and large vessel disease in European type 2 (non-insulin dependent) diabetic patients", Diabetologia (1991) 655-661.

Gallwitz, B. "Sitagliptin with Metformin: Profile of a Combination for the Treatment of Type 2 Diabetes". Drugs of Today, Oct. 2007, 43(10), p. 681-689.

Gallwitz, B. et al., "2-year efficacy and safety of linagliptin compared with glimepiride in patients with type 2 diabetes inadequately controlled on metformin: a randomised, double-blind, non-inferiority trial." Lancet, 2012, vol. 380, pp. 475-483.

Gallwitz, B. et al., "Saxagliptin, a dipeptidyl peptidase IV inhibitor for the treatment of type 2 diabetes". IDRUGS, vol. 11, No. 12, Dec. 2008, p. 906-917.

Gallwitz, B. et al., DPP IV inhibitors for the Treatment of Type 2 Diabetes; Diabetes Frontier (2007) vol. 18, No. 6 pp. 636-642.

Gallwitz, B., "Safety and efficacy of linagliptin in type 2 diabetes patients with common renal and cardiovascular risk factors." Therapeutic Advances in Endocrinology and Metabolism, 2013, vol. 4, No. 3, pp. 95-105.

Galvus (Vildagliptin) Scientific Discussion, EMEA, 2007, pp. 1-34.

Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.

Garber, A.J. et al., "Simultaneous glyburide/metformin therapy is superior to component monotherapy as an initial pharmacological treatment for type 2 diabetes." Diabetes, Obesity and Metabolism, 2002, vol. 4, pp. 201-208.

Sathananthan, A., et al., "Personalized pharmacotherapy for type 2 diabetes mellitus". Personalized Medicine 2009 Future Medicine Ltd, vol. 6, No. 4, Jul. 2009, p. 417-422.

Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.

Schillinger, M. et al., "Restenosis after percutaneous angioplasty: the role of vascular inflammation." Vascular Health and Risk Management, 2005, vol. 1, No. 1, pp. 73-78.

Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.

Schnapp, G. et al., "Analysis of Binding Kinetics and Thermodynamics of DPP-4 Inhibitors and their Relationship to Structure." 23rd PSDI, Protein Structure Determination in Industry, Tegernsee, Germany, Nov. 8-10, 2015.

Schnapp, G. et al., "Analysis of binding kinetics and thermodynamics of DPPIV Inhibitors and their relationship to structure." International Workshop: The aspect of time in drug design, Schloss Rauischholzhausen, Marburg, Germany, Mar. 24-27, 2014.

Schnapp, G. et al., "Comparative Enzyme Kinetic Analysis of the Launched DPP-4 Inhibitors." American Diabetes Association 74th Scientific Sessions, Poster 1048-P, 2014.

Schnapp, G. et al., "Comparative Enzyme Kinetic Analysis of the Launched DPP-4 Inhibitors." American Diabetes Association, Abstract 1048-P, 2014.

(56) References Cited

OTHER PUBLICATIONS

Schurmann, C. et al., "The Dipeptidyl Peptidase-4 Inhibitor Linagliptin Attenuates Inflammation and Accelerates Epithelialization in Wounds of Diabetic ob/ob Mice." The Journal of Pharmacology and Experimental Therapeutics, 2012, vol. 342, No. 1, pp. 71-80.
Schwartz, M. S. et al., "Type 2 Diabetes Mellitus in Childhood: Obesity and Insulin Resistance". JAOA Review Article, vol. 108, No. 9, Sep. 2008, p. 518.
Scientific Discussion, EMEA, Pramipexole, 2005, pp. 1-10.
Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).
Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.
Shanks, N. et al., Are animal models predictive for humans?, PEHM, Philosophy, Ethics, and Humanaities in Medicine, 4(2), 2009, 1-20.
Sharkovska, Y., et al., "DPP-4 Inhibition with Linagliptin Delays the Progression of Diabetic Nephropathy in db/db Mice." 48th EASD Annual Meeting, Berlin, Abstract 35, Oct. 2012.
Sheperd, Todd M. et al., "Efective management of obesity." The Journal of Family Practice, 2003, vol. 52, No. 1, pp. 34-42.
Shintani, Maki, et al., "Insulin Resistance and Genes" Circulatory Sciences (1997) vol. 17, No. 12 pp. 1186-1188.
Shu, L. et al., "Decreased TCF7L2 protein levels in type 2 diabetes mellitus correlate with downregulation of GIP- and GLP-1 receptors and impaired beta-cell function." Human Molecular Genetics, 2009, vol. 18, No. 13, pp. 2388-2399.
Shu, L. et al., "Transcription Factor 7-Like 2 Regulates B-Cell Survival and Function in Human Pancreatic Islets." Diabetes, 2008, vol. 57, pp. 645-653.
Silverman, G. et al., "Handbook of Grignard Reagents." 1996, Retrieved online: <http://books.google.com/books?id=82CaxfY-uNkC&printsec=frontcover&dq=intitle:Handbook+intitle:of+intitle:Grignard+intitle: Reagents&hl=en&sa=X&ei=g06GU5SdOKngsATphYCgCg&ved=0CDYQ6AEwAA#v=onepage&q&f=false>.
Singhal, D. et al., "Drug polymorphism and dosage form design: a practical perspective." Advanced Drug Delivery Reviews, 2004, vol. 56, pp. 335-347.
Sortino, M.A. et al., "Linagliptin: a thorough characterization beyond its clinical efficacy." Frontiers in Endocrinology, 2013, vol. 4, Article 16, pp. 1-9.
St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.
Stahl, P.H., "Handbook of Pharmaceutical Salts" C.G. Wermuth, Wiley-VCH, 2002, pp. 1-374.
Standl, E. et al., "Diabetes and the Heart." Diabetes Guidelines (DDG), 2002, pp. 1-25.
Sulkin, T.V. et al., "Contraindications to Metformin Therapy in Patients With NIDDM." Diabetes Care, 1997, vol. 20, No. 6, pp. 925-928.
Sune Negre, J. M. "New Galenic Contributions to Administration Forms". Continued Training for Hospital Pharmacists 3.2., (Publication date unavailable), Retrieved from internet on Feb. 23, 2011, http://www.ub.es/legmh/capitols/sunyenegre.pdf.
Suzuki, Y. et al., "Carbon-Carbon Bond Cleavage of a-Hydroxybenzylheteroarenes Catalyzed by Cyanide Ion: Retro-Benzoin Condensation Affords Ketones and Heteroarenes and Benzyl Migration Affords Benzylheteroarenes and Arenecarbaldehydes." Chemical Pharmaceutical Bulletin, 1998, vol. 46(2), pp. 199-206.
Tadayyon, M. et al., "Insulin sensitisation in the treatment of Type 2 diabetes." Expert Opinion Investigative Drugs, 2003, vol. 12, No. 3, pp. 307-324.

Takai, S. et al., "Significance of Vascular Dipeptidyl Peptidase-4 Inhibition on Vascular Protection in Zucker Diabetic Fatty Rats." Journal of Pharmacological Sciences, 2014, vol. 125, pp. 386-393.
Takeda Press Release: "Voglibose (BASEN) for the prevention of type 2 diabetes mellitus: A Randomized, Double-blind Trial in Japanese Subjects with Impaired Glucose Tolerance." 2008, Retrieved online Jul. 6, 2015. https://www.takeda.com/news/2008/20080526_3621.html.
Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.
Tanaka, S.. et al; "Suppression of Arthritis by the Inhibitors of Dipeptidyl Peptidase IV," In. J. Immunopharmac., vol. 19, No. 1, pp. 15-24, 1997.
Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.
Taskinen, M.-R. et al., "Safety and efficacy of linagliptin as add-on therapy to metformin in patients with type 2 diabetes: a randomized, double-blind, placebo-controlled study." Diabetes, Obesity and Metabolism, 2011, vol. 13, pp. 65-74.
Third Party Observation for application No. EP20070728655, May 13, 2013.
Thomas, L. et al, "BI 1356, a novel and selective xanthine beased DPP-IV inhibitor, exhibits a superior profile when compared to sitagliptin and vildagliptin." Diabetologia, 2007, vol. 50, No. Suppl. 1, p. S363.
Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.
Thomas, Leo et al: "(R)-8-(3-Amino-piperidin-1-yl)-7-but-2-ynyl-3-methyl-1- (4-methyl-quinazolin-2-ylmethyl)-3,7-dihydro-purine-2,6-dione (BI 1356), a Novel Xanthine-Based Dipeptidyl Peptidase 4 Inhibitor . . . " Journal of Pharmacology and Experimental Therapeutics, 2008, vol. 325, No. 1, pp. 177.
Thornber, C.W., "Isosterism and Molecular Modification in Drug Design." Chemical Society Reviews, 1979, pp. 563-580.
Tounyoubyou, "Symposium-19: Future Perspectives on Incretion Therapy in Diabetes." 2008, vol. 51, Suppl. 1, p. S-71, S19-2.
Tradjenta, Highlights of Prescribing Information (revised Sep. 2012).
Tribulova, N. et al. "Chronic Disturbances in NO Production Results in Histochemical and Subcellular Alterations of the Rat Heart." Physiol. Res., 2000, vol. 49, No. 1, pp. 77-88.
Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemic in type 2 Diabetic rats", J. Pharm Exp. 2011, vol. 339, No. 1, p. 228-237.
Tsuprykov, O. et al., Linagliptin is as Efficacious as Telmisartan in Preventing Renal Disease Progression in Rats with 5/6 Nephrectomy, 73rd Annual Meeting Science Session, ADA, Chicago, Jun. 2013.
Turner, R.C. et al., "Glycemic Control With Diet, Sulfonylurea, Metformin, or Insulin in Patients With Type 2 Diabetes Mellitus Progressive Requirement for Multiple Therapies (UKPDS 49)" The Journal of the American Medical Association, 1999, vol. 281, No. 21, pp. 2005-2012.
U.S. Appl. No. 15/235,575, filed Aug. 12, 2016, Inventor: Klaus DUGI. (The cited pending U.S. application is stored in the USPTO IFW system (MPEP 609.04(a)(II)(C)).
Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.

(56) References Cited

OTHER PUBLICATIONS

United Healthcare, "Diabetes." Retrieved from internet on Aug. 22, 2013, http://www.uhc.com/source4women/health_topics/diabetesirelatedinformation/dOf0417b073bf11OVgnVCM10-00002f1Ob1Oa_.htm.
Van Reek, M. et al., "Ezetimibe, a Potent Cholesterol Absorption Inhibitor, Normalizes Combined Dyslipidemia in Obese Hyperinsulinemic Hamsters." Diabetes, 2001, vol. 50, pp. 1330-1335.
Falanga, Lancet, Wound healing and impairment in the diabetic foot, vol. 366, 2005.
Who drug information, International nonproprietary Names for Pharmaceutical Substances, vol. 23, 2009.
Thielitz, Inhibitors of Dipeptidyl Peptidase IV and aminopeptidase N target Major Pathogenetic steps in Acne initiation, Journal of inventigative Dermatology, 2007.
Rai, Effect of Glycemic Control on apoptosis in diabetic wounds, Journal of Wound care, vol. 14, 2005.
Mcintosh, Dipeptidyl Synthase IV inhibitors, Regulatory Peptides, vol. 128, 2005.
Kaji, Dipeptidyl peptidase-4 inhibitor attenuates hepatic fibrosis via suppression of activated hepatic stellate cell in rats, J. Gastro, 2012.
Gorrell, Fibroblast Activation Protein, Handbook of Proteolytic Enzymes, 3rd ed., 2013.
McIennan, Molecular aspects of wound healing in diabetes, Dept. of Endocrinology, Univ of Sydney, vol. 14, 2006.
Pradham, Wound-healing abnormalities in Diabetes, Dept. of surgertm Harvard, Touch Briefings, 2007.
FDA Drug Safety Communication, FDA revises warnings regarding diabetes medicine metformin in certain patients with reduced kidney function, Apr. 8, 2016.
Groop, Diabetologica, 2012, vol. 55.
Basi, Diabetes Care, vol. 31, 2008.
Donnelly, BMJ, Vascular complications of diabetes, 2000.
Kendall, Emerging Treatments in Diabetes Care, Effects of Exenatide on Glycemic Control over 30 weeks in Patients with Type 2 Diabetes, vol. 28, 2005.
Sampanis, Hippokratia, Management of HypergIcemia in patients with diabetes mellitus and chronic renal failure, vol. 12, p. 22-27, 2008.
Hasanato, Diagnostic Efficacy of random albumin creatinine ration, Saudi Med, J., 2016, vol. 37.
Forst, The oral DPP 4 inhibitor linagliptin significantly lowers HbA1c after 4 weeks of treatment in patients with diabetes, Diabetes Obes Metab, vol. 13, 2011.
Garber, A.J. et al., "Update: Vildaglitin for the treatment of Type 2 diabetes" Expert Opinion on Investigational Drugs, 200801GB, vol. 17, No. 1, Jan. 2008, p. 105-113.
Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.
Geka, 2001, vol. 67, No. 11, p. 1295-1299.
Gennaro, Alfonso R. Remington Farmacia, 2003, Spanish copy: p. 828, English copy: pp. 711-712, Preformulation, Chapter 38.
Gennaro, Alfonso R., Remington Farmacia, 19th Edition, Spanish copy, 1995, p. 2470.
Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.
Gennaro, Alfonso; Remington: The Science and Practice of Pharmacy, Twentieth Edition, 2000, Chapter 45, pp. 860-869.
Giron, D.; Thermal Analysis and Calorimetric Methods in the Characterisation of Polymorphs and Solvates; Thermochimica Acta (1995) vol. 248 pp. 1-59.
GLUCOPHAGE® Prescribing Information, 2001.
Glucotrol XL (glipizide), package insert, Pfizer, Apr. 1, 2002.
Goldstein, L.A., et al., "Molecular cloning of seprase: a serine integral membrane protease from human melanoma." Biochimica et Biophysica Acta, vol. 1361, 1997, No. 1, pp. 11-19.

Gomez-Perez, et al, "Insulin Therapy:current alternatives", Arch. Med.Res. 36: p. 258-272 (2005).
Goodarzi, M.O. et al., "Metformin revisited: re-evaluation of its properties and role in the pharmacopoeia of modern antidiabetic agents." Diabetes, Obesity and Metabolism, 2005, vol. 7, pp. 654-665.
Graefe-Mody et al., "The novel DPP-4 inhibitor BI 1356 (proposed tradename ONDERO) and Metformin can be Safely Co-administered Without Dose Adjustment." Poster No. 553-P ADA Jun. 6-10, 2008, San Francisco http://professional.diabetes.org/content/posters/2008/p553-p. pdf.
Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
Graefe-Mody, U. et al.,0 "Effect of Renal Impairment on the Pharmacokinetics of the Dipeptidyl Peptidase-4 Inhibitor Linagliptin." Diabetes, Obseity and Metabolism, 2011, pp. 939-946.
Greene, T.W., et al., "Protection for the Amino Group". Protective Groups in Organic Synthesis, 3rd edition, 1999, p. 494-653.
Greischel, et al., Drug Metabolism and Deposition, "The Dipeptidyl Peptidase-4 Inhibitor Linagliptin Exhibits Time- and Dpse-Dependent Localization in Kidney, Liver, and Intestine after Intravenous Dosing: Results from High Resolution Autoradiography in Rats", 2010, vol. 38, No. 9, p. 1443-1448.
Groop, P.-H. et al., "Effects of the DPP-4 Inhibitor Linagliptin on Albuminuria in Patients with Type 2 Diabetes and Diabetic Nephropathy" 48th EASD Annual Meeting, Berlin, Abstract 36, Oct. 2012.
Guglielmi, C. et al., "Latent autoimmune diabetes in the adults (LADA) in Asia: from pathogenesis and epidemiology to therapy." Diabetes/Metabolism Research and Reviews, 2012, vol. 28, Supplement 2, pp. 40-46.
Gupta, V. et al., "Choosing a Gliptin." Indian Journal of Endocrinology and Metabolism, 2011, vol. 15, No. 4, pp. 298-308.
Gwaltney, S. "Medicinal Chemistry Approaches to the Inhibition of Dipeptidyl Peptidase IV", Current Topics in Medicinal Chemistry, 2008, 8, p. 1545-1552.
Gwaltney, S.L. II et al., "Inhibitors of Dipeptidyl Peptidase 4." Annual Reports in Medicinal Chemistry, 2005, vol. 40, pp. 149-165.
Hainer, Vojtech MD, PHD "Comparative Efficiency and Safety of Pharmacological Approaches to the Management of Obesity." Diabetes Care, 2011, vol. 34, Suppl. 2, pp. S349-S354.
Halimi, "Combination treatment in the management of type 2 diabetes: focus on vildagliptin and metformin as a single tablet", Vascular Health and Risk Management, 2008 481-92.
Halimi, S. et al., "Combination treatment in the management of type 2 diabetes: focus on vildagliptin and metformin as a single tablet." Vascular Health and Risk Management, 2008, vol. 4, No. 3, pp. 481-492.
Haluzik, M. et al., "Renal Effects of DPP-4 Inhibitors: A Focus on Microalbuminuria." International Journal of Endocrinology, 2013, vol. 35, No. 6, pp. 1-7.
Hammouda, Y. et al., "Lactose-induced Discoloration of Amino Drugs in Solid Dosage Form." Die Pharmazie, 1971, vol. 26, p. 181.
Hansen, H. et al., "Co-Administration of the DPP-4 Inhibitor Linagliptin and Native GLP-1 Induce Body Weight Loss and Appetite Suppression." 73rd Annual Meeting Science Session, ADA, Chicago, Jun. 21, 2013.
Hashida, Mitsuru, "Strategies for designing and developing oral administration formulations." Yakuji-Jiho, Inc., 1995, pp. 50-51.
Hayashi, Michio., "Recipe for Oral Hypoglycemic Agents to Pathological Condition" Pharmacy (2006) vol. 57, No. 9 pp. 2735-2739.
He, Y. L. et al., "Bioequivalence of Vildagliptin/Metformin Combination Tablets and Coadministration of Vildagliptin and Metforming as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.

(56) References Cited

OTHER PUBLICATIONS

He, Y.L. et al., "The influence of hepatic impariment on the pharmacokinetics f the dipeptidyl peptidase IV (DPP-4)Inhibitor vildagliptin" European Journal of Clinical Pharmacology, vol. 63, No. 7, May 8, 2007, p. 677-686.
He, Y.L. et al., "The Influence of Renal Impairment on the Pharmacokinetics of Vildagliptin." Clinical Pharmacology & Therapeutics, 2007, vol. 81, Suppl. 1, Abstract No. PIII-86.
Headland, K. et al., "The Effect of Combination Linagliptin and Voglibose on Glucose Control and Body Weight." 73rd Annual Meeting Science Session, ADA, Chicago, Jun. 21, 2013.
Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.
Heise, et al., Diabetes, Obesity and Metabolism, "Pharmacokinetics, pharmacokinetics and tolerability of mutilple oral doses of linagliptin, a dipeptidyl peptidase-4 inhibitor in male type 2 diabetes patients", 2009, vol. 11, No. 8, p. 786-794.
Heise, T. et al., "Treatment with BI 1356, a Novel and Potent DPP-IV Inhibitor, Significantly Reduces Glucose Excursions after an oGTT in Patients with Type 2 Diabetes." A Journal of the American Diabetes Association, Jun. 2007, vol. 56, Supplement 1, Poster No. 0588P.
Herman, G. A. et al., "Dipeptidyl Peptidase-4 Inhibitors for the Treatment of Type 2 Diabetes: Focus on Sitagliptin." Cinical Pharmacology and Therapeutics, 2007, vol. 81, No. 5, pp. 761-767.
Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.
Hermann, Robert, et al; Lack of Association of PAX4 Gene with Type 1 Diabetes in the Hungarian Populations; Diabetes (2005) vol. 54 pp. 2816-2819.
Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.
Hilfiker, R. et al., "Relevance of Solid-state Properties for Pharmaceutical Products." Polymorphism in the Pharmaceutical Industry, 2006, Chapter 1, pp. 1-19.
Hinke, S.A. et al., "Metformin Effects on Dipeptidylpeptidase IV Degradation of Glucagon-like Peptide-1." Biochemical and Biophysical Research Communications, 2002, vol. 291, No. 5, pp. 1302-1308.
Hinke, S.A. et al., "On Combination Therapy of Diabetes With Metformin and Dipeptidyl Peptidase IV Inhibitors." Diabetes Care, 2002, vol. 25, No. 8, pp. 1490-1492.
Hinnen, D. et al., "Incretin Mimetics and DPP-IV Inhibitors: New Paradigms for the Treatment of Type 2 Diabetes." Journal of The American Board of Family Medicine, 2006, vol. 19, No. 6, pp. 612-620.
Hocher, B. et al., "Renal and Cardiac Effects of DPP-4 Inhibitors—from Preclinical Development to Clinical Research." Kidney & Blood Pressue Research, 2012, vol. 36, No. 1, pp. 65-84.
Hocher, B. et al., "The novel DPP-4 inhibitors linagliptin and BI 14361 reduce infarct size after myocardial ischemia/reperfusion in rats." International Journal of Cardiology, 2013, vol. 167, pp. 87-93.
Holman, et al., "Addition of biphasic, prandial, or basal insulin to oral therapy in type 2 diabetes", N. England Journal Medicine, p. 1716-1730, 2007.
Horsford, E. N. "On the source of free hydrochloric acid in the gastric juice." Proceedings of the Royal Society of London, Published in 1868-1869, vol. 17, pp. 391-395.
International Search Report for PCT/EP2010/064691 dated Jan. 20, 2011.
International Search Report for PCT/EP2013/060309 dated Aug. 9, 2013.
International Search Report for PCT/EP2013/070979 dated Nov. 26, 2013.
International Search Report for PCT/EP2014/060160 dated Nov. 8, 2014.
Inukai, T., "Treatment of Diabetes in Patients for Whom Metformin Treatment is Not Appropriate." Modem Physician, 2008, vol. 28, No. 2, pp. 163-165.
Inzucchi, Silvio E., "Oral Antihyperglycemic Therapy for Type 2 Diabetes." The Journal of the American Medical Association, 2002, vol. 287, No. 3, pp. 360-372.
Isomaa, B. et al., "Cardiovascular Morbidity and Mortality Associated With the Metabolic Syndrome." Diabetes Care, 2001, vol. 24, No. 4, pp. 683-689.
Iwamoto, Yasuhiko, "Insulin Glargine." Nippon Rinsho, 2002, vol. 60, Suppl. 9, pp. 503-515.
Janumet Prescribing Information, revised Jan. 2008.
Januvia Medication Guide, 2010.
Januvia Prescribing Information and Product Label, 2006.
Januvia, 25mg, 50mg, 100 mg, Summary of Product Characteristics, 2015, www.medicines.org.uk/EMC <http://www.medicines.org.uk/EMC>.
Johansen, O. E. et al., "Cardiovascular safety with linagliptin in patients with type 2 diabetes mellitus: a pre-specified, prospective, and adjudicated meta-analysis of a phase 3 programme." Cardiovascular Diabetology, Biomed Central, 2012, vol. 11, No. 3, pp. 1-10.
Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www.abstractsonline.com, Jun. 10, 2012, XP-002708003.
John Hopkins Children's Center, "Liver Disorders and Diseases." Retrieved online May 26, 2014 <http://www.hopkinschildrens.org/non-alcoholic-fatty-liver-disease.aspx>.
Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.
Kanada, S. et al., "Safety, tolerability, pharmacokenetics and pharmacodynamics of multiple doses of BI 1356 (proposed tradename ONDERO), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.
Kelly. T., "Fibroblast activation protein-cx and dipeptidyl peptidase IV (CD26)P: Cell-surface proteases that activate cell signaling and are potential targets for cancern therapy". Drug Resistence Update 8, 2005, vol. 8. No. 1-2, pp. 51-58.
Kendall, D. M. et al., "Incretin Mimetics and Dipeptidyl Peptidase-IV Inhibitors: A Review of Emerging Therapies for Type 2 Diabetes." Diabetes Technology & Therapeutics, 2006, vol. 8, No. 3, pp. 385-398.
Kharkevich, D. A., "Educational Literature" Pharmacology (1987) Third Edition, Meditsina Press, Moscow pp. 47-48.
Kibbe, A., Editor. Handbook of Pharmaceutical Excipients, Third Edition, Copovidon—pp. 196-197, Date of Revision: Dec. 16, 2008.
Mannitol—pp. 424-425, Date of Revision: Feb. 19, 2009, Published in 2009.
Kidney Disease (Nephropathy), Retrieved online May 13, 2013. www.diabetes.org/living-with-diabetes/complications/kidney-disease-nephropathy.html <http://www.diabetes.org/living-with-diabetes/complications/kidney-disease-nephropathy.html>.
Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.
Kim, Kwang-Rok et al., "KR-62436, 6-{2-{2-(5-cyano4,5-dihydropyrazol-1-yl)-2-oxoethylamino}ethylamino} nicotinonitrile, is a novel dipeptidyl peptidase-IV (DDP-IV) inhibitor with anti-hyperglycemic activity" European Journal of Pharmacology 518, 2005, p. 63-70.

(56) References Cited

OTHER PUBLICATIONS

Kiraly, K. et al., "The dipeptidyl peptidase IV (CD26, EC 3.4.14.5) inhibitor vildagliptin is a potent antihyperalgesic in rats by promoting endomorphin-2 generation in the spinal cord." European Journal of Pharmacology, 2011, vol. 650, pp. 195-199.
Kirpichnikov, D. et al., "Metformin: An Update." Annals of Internal Medicine, 2002, vol. 137, No. 1, pp. 25-33.
Kishore, Preeti MD., "Complications of Diabetes Mellitus." Merck Manual Consumer Version, 2016, pp. 1-7.
Klein, T. et al., "Linagliptin alleviates hepatic steatosis and inflammation in a mouse model of non-alcoholic steatohepatitis." Medical Molecular Morphology, 2014, vol. 47, pp. 137-149.
Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.
Knowler, W.C. et al., "Reduction in the Incidence of Type 2 Diabetes with Lifestyle Intervention or Metformin." The New England Journal of Medicine, 2002, vol. 346, No. 6, pp. 393-403.
Komori, Kiyoshi., "Treatment of Diabetes in Patients for Whom Metforming Treatment is Not Appropriate" Modern Physician (2008) vol. 28, No. 2 pp. 163-165.
Konstantinou, D. M. et al., "Pathophysiology-based novel pharmacotherapy for heart failure with preserved ejection fraction." Pharmacology & Therapeutics, 2013, vol. 140, No. 2, pp. 156-166.
Korom, S. et al; Inhibition of CD26/dipeptidyl peptidase IV activity in vivo prolongs cardiac allograft survival in rat recipients1,2, Transplantation, May 27, 1997, vol. 63, No. 10, pp. 1495-1500.
Kroller-Scön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.
Kumar, V. et al., "Maillard Reaction and Drug Stability." Maillard Reactions in Chemistry, Food, and Health, 1994, No. 151, pp. 20-27.
Kuno, Y. et al., "Effect of the type of lubricant on the characteristics of orally disintegrating tablets manufactured using the phase transition of sugar alcohol." European Journal of Pharmaceutics and Biopharmaceutics, 2008, vol. 69, pp. 986-992.
Lachman, L. et al., "The Theory and Practice of Industrial Pharmacy." Varghese Publishing House, Third Edition, 1987, pp. 190-194.
Lakatos, P. L. et al., "Elevated Serum Dipeptidyl IV (CD26, EC 3.4.14.5) Activity in Experimental Liver Cirrhosis." European Journal of Clinical Investigation, 2000, vol. 30, No. 9, pp. 793-797.
Lakatos, P. L. et al., "Elevated serum dipeptidyl peptidase IV (CD26, EC 3.4.14.5) activity in patients with primary biliary cirrhosis." Journal of Hepatol, 1999, vol. 30, p. 740.
Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.
Lee Jones, K. et al., "Effect of Metformin in Pediatric Patients With Type 2 Diabetes." Diabetes Care, 2002, vol. 25, No. 1, pp. 89-94.
Leibovitz, E. et al., "Sitagliptin pretreatment in diabetes patients presenting with acute coronary syndrome: results from the Acute Coronary Syndrome Israeli Survey (ACSIS)." Cardiovascular Diabetology, 2013, vol. 12, No. 1, pp. 1-7.
Levien,T.L. et al, "New drugs in development for the treatment of diabetes", Diabetes Spectrum, American Diabetes Association, US, vol. 22, No. 2, Jan. 1, 2009, pp. 92-106.
Lieberman, H. et al., "Pharmaceutical Dosage Forms." Marcel Dekker, Inc., 1980, vol. 1, p. 38.
Lim, S. et al., "Effect of a Dipeptidyl Peptidase-IV Inhibitor, Des-Fluoro-Sitagliptin, on Neointimal Formation after Balloon Injury in Rats." Plos One, 2012, vol. 7, No. 4, pp. 1-11.
Linagliptin Monograph, Published by VACO PBM-SHG US Veteran's Administration, 2011, pp. 1-17.
Lindsay, J.R. et al., "Inhibition of dipeptidyl peptidase IV activity by oral metformin in Type 2 diabetes." Diabetic Medicine, 2005, vol. 22, pp. 654-657.
Lovshin, J.A. et al., "Incretin-based therapies for type 2 diabetes mellitus." Nature Reviews Endocrinology, 2009, vol. 5, pp. 262-269.
Lu, "High prevlaence of albuminuria in population based patients diagnosed with type 2 diabetes in the Shanghai downtown", Diabestes Research and Clinical Practice (2007) 184-192.
Lyssenko, V. et al., "Mechanisms by which common variants in the TCF7L2 gene increase risk of type 2 diabetes." The Journal of Clinical Investigation, 2007, vol. 117, No. 8, pp. 2155-2163.
Bundgaard, H. "Design of prodrugs: Bioreversible derivatives for various functional groups and chemical entities". Royal Danish School of Pharmacy, 1985, p. 1-92.
Busso et al., "Circulating CD26 is Negatively Associated with Inflammation in Human and Experimental Arthritis," Am. J. Path., vol. 166, No. 2, Feb. 2005, pp. 433-442.
Byrn, Stephen R. "Solid-State Chemistry of Drugs." Academic Press, 1982, pp. 1-27.
Caira, M.R., "Crystalline polymorphism of organic compounds" Topics in Current Chemistry, Springer, Berlin, vol. 198, 1998, p. 163-208.
Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.
Canadian Diabetes Association, "Pharmacologic Management of Type 2 Diabetes." Canadian Journal of Diabetes, 2003, vol. 27, Suppl. 2, pp. S37-S42.
Canadian Pharmacists Association, Compendium of Pharmaceuticals and Specialties, "Zestril" 2004, pp. 2289-2293.
Cao, C. et al., "The clinical application of linagliptin in Asians." Therapeutics and Clinical Risk Management, 2015, vol. 11, pp. 1409-1419.
Castello, R. et al., "Discoloration of Tablets Containing Amines and Lactose." Journal of Pharmaceutical Sciences, 1962, vol. 51, No. 2, pp. 106-108.
Chan, J.C. et al., "Safety and efficacy of sitagliptin in patients with type 2 diabetes and chronic renal insufficiency." 2008, Diabetes, Obesity and Metabolism, vol. 10, pp. 545-555.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Chaykovska, L. et al., "Effects of DPP-4 Inhibitors on the Heart in a Rat Model of Uremic Cardiomyopathy." www.plosone.org, 2011, vol. 6, No. 11, p. e27861.
ChemGaroo, "Leaving Group." 1999, Retrieved online: http://www.chemgapedia.de/vsengine/vlu/vsc/en/ch/12/oc/vluorganik/substitution/sn_2/sn 2. vlu/Page/vsc/en/ch/12/oc/substitution/sn_2/abgangsgrupen/abgangsgruppe. vscml. html.
Chemical Abstract. EP412358, 1991:185517, Findeisen.
Chemical Abstract: FR2707641, 1995:543545, Dodey.
Chemical Abstract: No. 211513-37-0—Dalcetrapib. "Propanethioic acid, 2-methyl-,S-(2-[[[1-(2-ethylbutyl)cyclohexyl}carbonyl}amino}pheyl}ester". Formula: C23 H35 N O2 S. American Chemical Society. Sep. 20, 1998.
Chemical Abstract: No. 875446-37-0—Anacetrapib. "2-Oxazolidinone, 5-[3,5-bis(trifluoromethyl)phenyl]-3[[4'fluoro-2'-methoxy-5'-(1-methylethyl)-4-(trifluoromethyl)[1,1'-biphenyl]-2-yl]methyl]-4-methyl-,(4S,5R)-" Formula: C30 H25 F10 N O3. American Chemical Society, Feb. 28, 2006.
Chemical Abstracts Accession No. 106:95577 Romanenko et al., "Synthesis and Biological Activity of 3-Methyl, 7-or 8-alkyl-8-dialkyl, heterocyclic, and cyclohexylaminoxanthines," Zaporozh. Med. Institute (1986).
Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.

(56) References Cited

OTHER PUBLICATIONS

Chemical Abstracts Service, Database Accession number No. RN 668270-12-01, 2004, "1H-Purine-2,6-dione, 8-[(3R)-3-amino-1-piperidinyl]-7-(2-butyn-1-yl)-3,7-dihydro-3-methyl-1-[(4-methyl-2-quinazolinyl)methyl]".
Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, http://www.accessdata.fda.gov/drugsatfda_docs/nda/2011/201280Orig1s000ChemR.pdf.
Cheon, et al., Biochemical Pharmacology, "Inhibition of dipeptidyl IV by novel inhibitors with pyrazolidine scaffold", 2005, vol. 70, p. 22-29.
Chiasson, J.-L. et al., "The Synergistic Effect of Miglitol Plus Metformin Combination Therapy in the Treatment of Type 2 Diabetes." Diabetes Care, 2001, vol. 24, No. 6, pp. 989-994.
Chisari, A. et al. "Sulphinyl, Sulphonyl, and Sulphonium Groups as Leaving Groups in Aromatic Nucleophilic Substitutions." Journal of the Chemical Society, Perkin Transactions II, 1982, pp. 957-959.
Chowhan, Z.T. et al., Drug-Excipient Interaction Resulting from Powder Mixing IV: Role of Lubricants and Their Effect on In Vitro Dissolution, Journal of Pharmaceutical Sciences, 1986, vol. 75, No. 6, pp. 542-545.
Clinical Trial NCT00622284 (published online at clinicaltrials.gov on Feb. 22, 2008).
Clinical Trial Protocol, "A Randomised, Double-blind, Placebo-controlled, Five Parallel Groups Study Investigating the Efficacy and Safety of BI 1356 BS." Boehringer Ingelheim Pharmaceuticals, last updated on Jun. 24, 2014.
Clinical Trial, NCT00622284, clinicaltrials.gov, updated Feb. 22, 2008.
clinical Trials NCT00601250, clinicaltrials.gov, Jan. 25, 2008.
Clinical Trials, No. NCT00309608, "Efficacy and Safety of BI 1356 BS in Combination with Metformin in Patients With Type2 Diabetes" 2009, pp. 1-3.
Clinical Trials, No. NCT00622284, "Efficacy and Safety of BI 1356 in combination with metformin in patients with type 2 diabetes" 2012, pp. 1-5.
Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCT00601250/2008_01_25 [retrieved on Feb. 27, 2009].
Clinical Trials. NCT0622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.
Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.
Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.
Clinical Trials: NCT00103857, "A Multicenter, Randomized, Double-Blind Factorial Study of the Co-Administration of MK0431 and Metformin in Patients With Type 2 Diabetes Mellitus Who Have Inadequate Glycemic Control" last updated on Apr. 27, 2015.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated on Jun. 24, 2014.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated: Dec. 11, 2013.
Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov. http://clinicaltrials.gov/archive/NCT00309608/2009_01_27.
Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.
Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.
Clinical Trials: NCT00798161. "Safety and efficacy of Bi 1356 Plus Metformin in Type 2 Diabetes, Factorial Design". Clinical Trials.gov archive. A Service of the U.S> National Institutes of Health. Nov. 24, 2008, p. 1-3. http://clinicaltrials.gov/archive/NCT00798161/2008_11_24.
Colorcon, "Lactose Replacement with Starch 1500 in a Direct Compression Formula." 2005, pp. 1-4.
Colorcon, "Reducing Coated Tablet Defects from Laboratory through Production Scale: Performance of Hypromellose or Polyvinyl Alcohol-Based Aqueous Film Coating Systems." Opadry II, 2009, pp. 1-7.
Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.
Conarello, S.L. et al., "Mice lacking dipeptidyl peptidase IV are protected against obesity and insulin resistance". PNAS, May 27, 2003, vol. 100, No. 11, p. 6825-6830.
Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.
Cotton, M.L. et al., "L-649,923—The selection of an appropriate salt form and preparation of a stable oral formulation." International Journal of Pharmaceutics, 1994, vol. 109, Issue 3, pp. 237-249.
Craddy, P. et al., "Comparative Effectiveness of Dipeptidylpeptidase-4 Inhibitors in Type 2 Diabetes: A Systematic Review and Mixed Treatment Comparison." Diabetes Therapy, 2014, vol. 5, No. 1, pp. 1-41.
Crowe, E. et al., "Early identification and management of chronic kidney disease: summary of NICE guidance." British Medical Journal, 2008, vol. 337, pp. 812-815.
"Betahistine diHCL CF 16 mg, tabletten," Dutch Medicines Evaluation Board, Dated Apr. 13, 1988, Retrieved online from: <http://db.cbg-meb.nl/ords/f?p=111:3:0:SEARCH:NO::P0_DOMAIN,P0_LANG,P3_RVG1:H,EN,57626>.
"Betahistine diHCL CF 8 mg, tabletten," Dutch Medicines Evaluation Board, Dated Apr. 13, 1988, Retrieved online from: <http://db.cbg-meb.nl/ords/f?p=111:3:0:SEARCH:NO::P0_DOMAIN,P0_LANG,P3_RVG1:H,EN,56227>.
"Sifrol 0,088 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70120>.
"Sifrol 0,18 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:11,EN,70121>.
"Sifrol 0,35 mg, tabletten," Dutch Medicines Evaluation Board, Dated Nov. 16, 1999, Retrieved online from: <http://db.cbg-meb.nl/ords/f?p=111:3:0-SEARCH:NO::P0_DOMAIN,P0_LANG,P3_RVG1:H,EN,70673>.
"Sifrol 0,70 mg, tabletten," Dutch Medicines Evaluation Board, Dated Oct. 14, 1997, Retrieved online from: <http://db.cbg-meb.nl/ords/f?p=111:3:0-SEARCH:NO::P0_DOMAIN,P0_LANG,P3_RVG1:H,EN,70122>.
"Sifrol 1,1 mg, tabletten," Dutch Medicines Evaluation Board, Dated Oct. 14, 1997, Retrieved online from: <http://db.cbg-meb.nl/ords/f?p=111:3:0-SEARCH:NO::P0_DOMAIN,P0_LANG,P3_RVG1:H,EN,70124>.
Abstract for AU 2003280680, Jun. 18, 2004.
Abstract for AU 2009224546, Sep. 17, 2009.
Abstract in English for DE10109021, 2002.
Abstract in English for DE19705233, Aug. 13, 1998.
Abstract in English for DE2205815, 1972.

(56) References Cited

OTHER PUBLICATIONS

Abstract in English for EP0023032, 1981.
Abstract in English for JP 2002/348279, Dec. 4, 2002.
Abstract in English for JP 2003/286287, Oct. 10, 2003.
Abstract in English for KR20070111099, Nov. 11, 2007.
Actos Prescribing Information, 1999, pp. 1-26.
Adebowale, K.O. et al., "Modification and properties of African yam bean (Sphenostylis stenocarpa Hochst. Ex A. Rich.) Harms starch I: Heat moisture treatments and annealing." Food Hydrocolloids, 2009, vol. 23, No. 7, pp. 1947-1957.
Ahren, B. et al., "Twelve- and 52-Week Efficacy of the Dipeptidyl Peptidase IV Inhibitor LAF237 in Metformin-Treated Patients With Type 2 Diabetes." Diabetes Care, 2004, vol. 27, No. 12, pp. 2874-2880.
Ahren, Bo "Novel combination treatment of type 2 diabetes DPP-4 inhibition + metformin." Vascular Health and Risk Management, 2008, vol. 4, No. 2, pp. 383-394.
Ahren, Bo, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Ahren, Bo; "DPP-4 inhibitors", Best practice and research in clinical endocrinology and metabolism—New therapies for diabetes 200712 GB LNKD- DOI:10.1016/J. Beem.2007.07.005, vol. 21, No. 4, Dec. 2007, pp. 517-533.
Al-Masri, I.M. et al., "Inhibition of dipeptidyl peptidase IV (DPP IV) is one of the mechanisms explaining the hypoglycemic effect of berberine." Journal of Enzyme Inhibition and Medicinal Chemistry, 2009, vol. 24, No. 5, pp. 1061-1066.
Alter, M. et al., "DPP-4 Inhibition on Top of Angiotensin Receptor Bockade Offers a New Therapeutic Approach for Diabetic Nephropathy" Kidney and Blood Pressue Research, 2012, vol. 36, No. 1, pp. 119-130.
American Association of Clinical Endocrinologists, "Medical Guidelines for Clinical Practice for the Management of Diabetes Mellitus." Endocrine Practice, 2007, col. 13, Suppl. 1, pp. 1-68.
American Diabetes Association, "Standards of Medical Care in Diabetes-2008." Diabetes Care, Jan. 2008, vol. 31, Supplement 1, pp. S12-S54.
Anstee, Quentin M. et al. "Mouse models in non-alcholic fatty liver disease and steatohepatitis research" (2006) International Journal of Expermental Pathology, vol. 87, pp. 1-16.
Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.
Augusti, D.V. et al., "Quantitative determination of the enantiomeric composition of thalidomide solutions by electrospray ionizatio tandem mass spectrometry". Chem Comm, 2002, p. 2242-2243.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Aulinger, B.A. et al., "Ex-4 and the DPP-IV Inhibitor Vildagliptin have Additive Effects to Suppress Food Intake in Rodents". Abstract No. 1545-P, 2008.
Aulton, Michael E., Pharmaceutics: The Science of Dosage Form Design, Second Edition, 2002, pp. 441-448.
Baetta, R. et al., "Pharmacology of Dipeptidyl Peptidase-4 Inhibitors." Drugs, 2011, vol. 71, No. 11, pp. 1441-1467.
Balaban, Y.H.et al., "Dipeptidyl peptidase IV (DDP IV) in NASH patients" Annals of Hepatology, vol. 6, No. 4, Oct. 1, 2007, pp. 242-250, abstract.
Balbach, S. et al., "Pharmaceutical evaluation of early development candidates the 100 mg-approach." International Journal of Pharmaceutics, 2004, vol. 275, pp. 1-12.
Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.

Banker, Gilbert S., "Prodrugs." Modern Pharmaceutics Third Edition, Marcel Dekker, Inc., 1996, p. 596.
Bastin, R.J. et al., "Salt Selection and Optimization Procedures for Pharmaceutical New Chemical Entities". Organic Process Research and Development, 2000, vol. 4, p. 427-435.
Beauglehole, Anthony R., "N3-Substituted Xanthines as Irreversible Adenosine Receptor Antagonists." Ph.D. Thesis, Deakin University, Australia, 2000, pp. 1-168.
Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.
Berge, S. et al., "Pharmaceutical Salts." Journal of Pharmaceutical Sciences, 1977, vol. 66, No. 1, pp. 1-19.
Bernstein, Joel "Polymorphism in Molecular Crystals." Oxford University Press, 2002, p. 9.
Blech, S. et al., "The Metabolism and Disposition of the Oral Dipeptidyl Peptidase-4 Inhibitor, Linagliptin, in Humans", Drug Metabolism and Disposition, 2010, vol. 38, No. 4, p. 667-678.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Borloo, M. et al. "Dipeptidyl Peptidase IV: Development, Design, Synthesis and Biological Evaluation of Inhibitors." 1994, Universitaire Instelling Antwerpen, vol. 56, pp. 57-88.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Boulton, D.W. et al., "Safety, Tolerability, Pharmacokinetics and Pharmacodynamics of Once-Daily Oral Doses of Saxagliptin for 2 Weeks in Type 2 Diabetic and Healthy Subjects." Diabetes, 2007, Supplement 1, vol. 56, pp. A161.
Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Brittain, H.G., "Methods for the Characterization of Polymorphs: X-Ray Powder Diffraction," Polymorphism in Pharmaceutical Solids, 1999, p. 235-238.
March, J. "Advanced Organic Chemistry: Reactions, Mechanisms, and Structure". Fourth Edition, 1992, pp. 652-653.
Mathieu, C. et al., "Antihyperglycaemic therapy in elderly patients with type 2 diabetes: potential tole of incretin mimetics and DPP-4 inhibitors." International Journal of Clinical Practice, 2007, vol. 61, Suppl. 154, pp. 29-37.
Matsumiya, Teruhiko, et al., "Therapeutic Drugs for Clinicians" Diagnosis and Treatment (2008) vol. 96, No. 2 pp. 389-390.
Mayo Clinic Staff: "Nonalchoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.
McNay, David E.G. et al., "High fat diet causes rebound weight gain." Molecular Metabolism, 2013, vol. 2, pp. 103-108.
Medline Plus, "Obesity" 2013, Retrieved from internet on Aug. 22, 2013, http://www.nlm.nih.gov/medlineplus/obesity.html.
Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.
Mendes, F.D, et al. "Recent advances in the treatment of non-alcoholic fatty liver disease". Expert Opinion on Investigational Drugs, vol. 14, No. 1, Jan. 1, 2005, p. 29-35.
Merck Manual of Diagnosis and Therapy: "Obesity." 1999, 17th Edition, Chapter 5, pp. 58-62.
Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?ald=96695.

(56) References Cited

OTHER PUBLICATIONS

Mikhail, Nasser, "Incretin mimetics and dipeptidyl peptidase 4 inhibitors in clinical trials for the treatment of type 2 diabetes." Expert Opinion on Investigational Drugs, 2008, vol. 17, No. 6, pp. 845-853.
MIMS Jan. 2009, "Sitagliptin." pp. 152-153.
Moritoh, Y. et al., "Combination treatment with alogliptin and voglibose increases active GLP-1 circulation, prevents the development of diabetes and preserves pancreatic beta-cells in prediabetic db/db mice." Diabetes, Obesity and Metabolism, 2010, vol. 12, pp. 224-233.
Nabors, Lyn O'Brien "Alternative Sweeteners." Marcel Dekker, Inc., 2001, pp. 235, 339-340.
Naik, R. et al., "Latent Autoimmune Diabetes in Adults." The Journal of Clinical Endocrinology and Metabolism, 2009, vol. 94, No. 12, pp. 4635-4644.
Nar, Herbert "Analysis of Binding Kinetics and Thermodynamics of DPP-4 Inhibitors and their Relationship to Structure." 2nd NovAliX Conference: Biophysics in drug discovery, Strasbourg, France, Jun. 9-12, 2015.
Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.
National Program for Care Guidelines, "Type 2 Diabetes mellitus." 2002, First Edition, pp. 1-50.
Nauck, M. A. et al., "Efficacy and Safety of Adding the Dipeptidyl Peptidase-4 Inhibitor Alogliptin to Metformin Therapy in Patients with Type 2 Diabetes Inadequately Controlled with Metformin Monotherapy: A Multicentre, Randomised, Double-Blind, Placebo-Cotrolled Study." Clinical Practice, 2008, vol. 63, No. 1, pp. 46-55.
Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." Diabetes Obesity and Metabolism, 2007, vol. 9, No. 2, pp. 194-205.
Nielsen, L., "Incretin Mimetics and DPP-IV Inhibitors for the Treatment of Type 2 Diabetes." Drug Discovery Today, 2005, vol. 10, No. 10, pp. 703-710.
Nihon Ijinpo, Japan Medicinal Journal, 2001, No. 4032, p. 137.
Novartis AG, Investor Relations Release, "Galvus, a new oral treatment for type 2 diabetes, receives positive opinion recommending European Union approval." Securities and Exchange Commission, Form 6-K, 2007, pp. 1-4.
O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.
Office Action for U.S. Appl. No. 10/695,597 dated May 2, 2008.
Oz, Helieh S., "Methionine Deficiency and Hepatic Injury in a Dietary Steatohepatitis Model." Digestive Diseases and Sciences, 2008, vol. 53, No. 3, pp. 767-776.
Patani George A. et al.: "Bioisoterism : A Rational Approach in Drug Design", Chemical Reviews, 1996, vol. 96, No. 8, pp. 3147-3176.
Pearson, E. R. et al., "Variation in TCF7L2 Influences Therapeutic Response to Sulfonylureas." Diabetes, 2007, vol. 56, pp. 2178-2182.
Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.
Pietruck, F. et al., "Rosiglitazone is a safe and effective treatment option of new-onset diabetes mellitus after renal transplantation." Transplant International, 2005, vol. 18, pp. 483-486.
Pilgaard, K. et al., "The T allele of rs7903146 TCF7L2 is associated with impaired insulinotropic action of incretin hormones, reduced 24 h profiles of plasma insulin and glucagon, and increased hepatic glucose production in young healthy men." Diabetologia, 2009, vol. 52, pp. 1298-1307.
Plummer, C.J.G. et al., "The Effect of Melting Point Distributions on DSC Melting Peaks." Polymer Bulletin, 1996, vol. 36, pp. 355-360.
Pospisilik, et al; Dipeptidyl Peptidase IV Inhibitor Treatment Stimulates ?—Cell Survival and Islet Neogenesis in Streptozotocin-Induced Diabetic Rats; Diabetes, vol. 52, Mar. 2003 pp. 741-750.
Poudel, Resham R., "Latent autoimmune diabetes of adults: From oral hypoglycemic agents to early insulin." Indian Journal of Endocrinology and Metabolism, 2012, vol. 16, Supplement 1, pp. S41-S46.
Pratley, R. et al., "Inhibition of DPP-4: a new therapeutic approach for the treatment of type 2 diabetes." Current Medical Research and Opinion, 2007, vol. 23, No. 4, pp. 919-931.
Prescribing Information, Package insert for Leprinton tablets 100mg, Manufacturer: Tatsumi Kagaku Co., Ltd., Mar. 2003, pp. 1-3.
Priimenko, B. A., et al; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.
Radermecker, Regis et al., "Lipodystrophy Reactions to Insulin." American Journal of Clinical Dermatology, 2007, vol. 8, pp. 21-28.
Rask-Madsen, C. et al., "Podocytes lose their footing." Nature, 2010, vol. 468, pp. 42-44.
Rhee et al.: "Nitrogen-15-Labeled Deoxynucleosides. 3. Synthesis of [3-15N]-2'-Deoxyadenosine" J. Am. Chem. Soc. 1990, 112, 8174-8175.
Rosenbloom, et al., "Type 2 Diabetes mellitus in the child and adolescent", Pediatric Diabetes, 2008, p. 512-526.
Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.
Rosenstock, et al., Sitagliptin Study 019 Groups, Efficacy and safety of the dipeptidyl peptidase-4 inhibitor sitagliptin, Clinical Therapeutics, 2006, vol. 28, Issue 10, p. 1556-1568.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Rosenstock, J. et al., "Triple Therapy in Type 2 Diabetes." Diabetes Care, 2006, vol. 29, No. 3, pp. 554-559.
Rowe, R. et al., Handbook of Pharmaceutical Excipients, Fifth Edition, Pharmaceutical Press, 2006, pp. 389-395, 449-453, and 731-733.
Rowe, R. et al., Handbook of Pharmaceutical Excipients, Fourth Edition, Pharmaceutical Press and American Pharmaceutical Association, 2003, pp. 323-332.
Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.
Salomon, J., et al; Ultraviolet and g-Ray-Induced Reactions of Nucleic Acid Constituents. Reactions of Purines with Amines; Photochemistry and Photobiology (1974) vol. 19 pp. 21-27.
Sarafidis, P. et al., "Cardiometabolic Syndrome and Chronic Kidney Disease: What is the link?" JCMS 2006, 1: p. 58-65.
Merck Index, 15th Ed., Linagliptin, 2013.
Janumet dosing instructions, Highlights of Prescribing information, 2008.
Ennis, Handbook of Pharmaceutical Granulation Technology, Theory of Granulation, 2010.
Houben-Weyl, Oxygen Compounds, Methods of Organic Chemistry, 1929.
Slotta, On Biguanides, Chem. Institute at the Univ. of Wroclaw, vol. 62, 1929.
Laugesen, Latent Autoimmune diabetes of the adult: current knowledge and uncertainty, vol. 10, 2015., Diabetic medicine.
Johansen, Diabetes Care, C-peptide Levels in latent Autoimmmune Diabetes in Adults treated with Linagliptin vs. Glimepiride, vol. 37, 2014.

(56) References Cited

OTHER PUBLICATIONS

Drucker, Glucagon-like peptide I stimulates insulin gene expression and increases cyclic AMP levels in a rat islet cell line, Proc. Natl. Acad. Sci, vol. 84, a97.
Mojsov, Insulintropin: Glucagin like peptide: Lab of Molecular Endocrinology, vol. 79, 1987, p. 616-619.
Holst,Role on incretin hormones in the regulation of insulin, Am j. Physiol Endocrinol Metab., 2004.
Matsuyama, Glucagen like peptide: a ptotent glucagonostatic hormone, Diabetes Research, 1988, p. 281-288.
Wettergren, Truncated GLP-1, Inhibits Pancreatic and Gastric Functions in Man, 1993, p. 665-673.
Li, Glucagen like Peptide 1 Receptor Signaling Modulates b cell apoptosis, Journal of Biological Chem, 2003.
Drug Data Report, 1994, Source, Smith Kline Beechman, Treatments for Septic Shock, p. 459.
Horie, Biomedcentral, Design, statistical analsysis and sample size calculation of a phase IIb/III study of linagliptin vs. voglibose and placebo, 2009.
International Search report for PCT/EP2019/069126, dated Oct. 2, 2019.
Press, Synthesis of 5,6 Dimethoxyquinazolin-2(1-H) ones, J. Heterocyclic Chwm, 1986.
Adams, Pub Pharmafile, 2011, Boehringer-lilly launch diabetes drug tradjenta in US.
Excerpt from Orange Book of Product Tradjenta, Feb. 5, 2011.
Roy, Pharmaceutical Impurities, PharmSciTech, 2002.
Publication Boehringer Ingelheim and Lilly's New type 2 Diabetes Treatment tradjenta, 2015, p. 1-7.
Donelly, Vascular Complications of Diabetes, MBJ, vol. 320, 2000.
Smithies, The Jackson Lab, Mouse Strain Datasheet, 2019, p. 1-2.
American Diabetes Assoc., Diagnosis and Classification of Diabetes Mellitus, vol. 29, 2006.
Deshpande, American Physical Therapy Assoc., Epidemiology of Diabetes related complications, 2008, vol. 88.
Vichayanrat, A. et al., "Efficacy and safety of voglibose in comparison with acarbose in type 2 diabetic patients." Diabetes Research and Clinical Practice, 2002, vol. 55, pp. 99-103.
Vickers, 71st Scientific Session of the American Diabetes Association, "The DPP-4 inhibitor linagliptin is weight neutral in the DIO rat but inhibits the weight gain of DIO animals withdrawn from exenatide", vol. 60, Jul. 2011.
Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.
Villhauer, E.B., et al., "1-{2-{5-Cyanopyridin-2-yl)amino}-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.
Vincent, S.H. et al., "Metabolism and Excretion of the Dipeptidyl Peptidase 4 Inhibitor [14C]Sitagliptin in Humans." Drug Metabolism and Disposition, 2007, vol. 35, No. 4, pp. 533-538.
Wang, Y. et al., "BI-1356. Dipeptidyl-Peptidase IV Inhibitor, Antidiabetic Agent." Drugs of the Future, 2008, vol. 33, No. 6, pp. 473-477.
Weber, Ann E., "Dipeptidyl Peptidase IV Inhibitors for the Treatment of Diabetes." Journal of Medicinal Chemistry, 2004, vol. 47, pp. 4135-4141.
WebMD, Autoimmune Diseases: What Are They? Who Gets Them? "What Are Autoimmune Disorders?" 2015, pp. 1-3. Retrieved online Jul. 9, 2015. http://www.webmd.com/a-to-z-guides/autoimmune-diseases.
Wertheimer, et al., "Drug Delivery Systems improve pharmaceutical profile and facilitate medication adherence", Adv. Therapy 22: p. 559-577 (2005).
White, John R. Jr., "Dipeptidyl Peptidase-IV Inhibitors: Phamacological Profile and Clinical Use". Clinical Diabetes, Apr. 2008, vol. 26, No. 2, pp. 53-57.
Wikipedia, "Linagliptin" Sep. 12, 2015. <https://en.wikipedia.org/w/index.php?title=Linagliptin&oldid=333469979>.
Wikipedia, Annulation. Jun. 23, 2008, http://en.wikipedia.org/wiki/Annelation.
Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.
Wirth, D. et al., "Maillard Reaction of Lactose and Fluoxetine Hydrochloride, a Secondary Amine." Journal of Pharmaceutical Sciences, 1998, vol. 87, No. 1, pp. 31-39.
Witteles, R. M. et al., "Dipeptidyl Peptidase 4 Inhibition Increases Myocardial Glucose Uptake in Nonischemic Cardiomyopathy." Journal of Cardiac Failure, 2012, vol. 18, No. 10, pp. 804-809.
Wolff, M.E.: "Burger's Medicinal Chemistry and Drug Discovery" Fifth Edition, vol. 1: Principles and Practice, pp. 975-977, 1994, John Wiley & Sons, Inc.
World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.
X-Ray Diffraction. The United States Pharmacopeia, 2002, USP 25 NF20, p. 2088-2089.
Yale, Jean-Francois, "Oral Antihyperglycemic Agents and Renal Disease: New Agents, New Concepts." Journal of the American Society of Nephrology, 2005, vol. 16, Suppl. 1, pp. S7-S10.
Yamagishi, S. et al., "Pleiotropic Effects of Glucagon-like Peptide-1 (GLP-1)-Based Therapies on Vascular Complications in Diabetes." Current Pharmaceutical Design, 2012, vol. 17, pp. 4379-4385.
Yap, W.S. et al., "Review of management of type 2 diabetes mellitus." Journal of Clinical Pharmacy and Therapeutics, 1998, vol. 23, pp. 457-465.
Yasuda, et al. "E3024 3-but-2-ynyl-5-methyl-2-piperazin-1-yl-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.
Yasuda, N. et al., "Metformin Causes Reduction of Food Intake and Body Weight Gain and Improvement of Glucose Intolerance in Combination with Dipeptidyl Peptidase IV Inhibitor in Zucker fa/fa Rats." The Journal of Pharmacology and Experimental Therapeutics, 2004, vol. 310, No. 2, pp. 614-619.
Yokoyama< "Prevalence of albumineria and renal insufficiency and associated clinical factors in type 2 diabetes: the Japan Diabetes clinical data Management study(JDDM15)" Nephrol Dial Transplant (2009) 24: 1212-1219 Advance Access Pub 2008.
Yoshikawa, Seiji et al.: Chemical Abstract of Japanese Patent No. WO 2003/104229 Preparation of purinone derivatives as dipeptidylpeptidase IV (DPP-IV) inhibitors, 2003.
Yoshioka, S. et al., "Stability of Drugs and Dosage Forms." Kluwer Academic Publishers, 2002, pp. 30-33.
Youssef, S. et al., "Purines XIV. Reactivity of 8-Promo-3,9-dimethylxanthine Towards Some Nucleophilic Reagents." Journal of Heterocyclic Chemistry, 1998, vol. 35, pp. 949-954.
Zander, M. et al., "Additive Glucose-Lowering Effects of Glucagon-Like Peptide-1 and Metformin in Type 2 Diabetes." Diabetes Care, 2001, vol. 24, No. 4, pp. 720-725.
Zeeuw, D. et al., "Albuminuria, a Therapeutic Target for Cardiovascular Protection in Type 2 Diabetic Patients With Nephropathy." Circulation, 2004, vol. 110, No. 8, pp. 921-927.
Zejc, Alfred, et al; "Badania Nad Piperazynowymi Pochodnymi Dwumetyloksantyn" Acta Polon Pharm, XXXV (1976) Nr. 4 pp. 417-421.
Zerilli, T. et al., "Sitagliptin Phosphate: A DPP-4 Inhibitor for the Treatment of Type 2 Diabetes Mellitus." Clinical Therapeutics, 2007, vol. 29, No. 12, pp. 2614-2634.
Zhimei, Xiao et al., "Study progression of oral drugs for treatment of type II diabetes." Drug Evaluation, 2004, vol. 1, No. 2, pp. 138-143.

(56) References Cited

OTHER PUBLICATIONS

Zhong, Qing et al; "Glucose-dependent insulinotropic peptide stimulates proliferation and TGF-? release from MG-63 cells," Peptides 24 (2003) 611-616.
Zhu, G. et al., "Stabilization of Proteins Encapsulated in Cylindrical Poly(lactide-co-glycolide) Implants: Mechanism of Stabilization by Basic Additives." Pharmaceutical Research, 2000, vol. 17, No. 3, pp. 351-357.
Zimdahl, H. et al., "Influence of TCF7L2 gene variants on the therapeutic response to the dipeptidylpeptidase-4 Inhibitor linagliptin." Diabetologia, 2014, vol. 57, pp. 1869-1875.
Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.
Jibiinkoka-Tenbo, Vision of Otorhinolaryngology, How to use antimicrobial drug in a patient with impairment of renal function, vol. 44, No. 3, 2001, p. 217-220.
Rinsho-Yakuri, Jpn. J. Clin. Pharmacol. Ther. Pharmacokinetics: excretion, 30(3) 1999.
Fiorucci, et al. Trends in Molecular Medicine, Targeting farnesoid X receptor for liver and metabolic disorders, 13(7), 2007, p. 298-309.
Morhenn, "Keratinacyte proliferation n wound healing and skin diseases", Immunology Today, vol. 9, Issue 4, 1988, p. 104.
*Boehringer Ingelheim Pharmceuticals, Inc.* v. *HEC Pharm Co., Ltd., et al.*, No. 15-cv-5982, United States District Court for the District of New Jersey, Dec. 8, 2016.
Karaliede et al, Diabetes Care, Endothelial Factors and Diabetic Nephropathy, 2011, 34, Suppl 2, p. 291-296.
Hansen, European Journal of Pharmacology, "The DPP-IV inhibitor linagliptin and GLP-1 induce synergistic effects on body weight loss and appetite suppression in the diet-induced obese rat", 2014, p. 254-263.
Ferreira, Triple Combination therapy with sitagliptin, metformin and rosiglitazone improves glycaemic control in patiens with type 2 diabetes, Diabetologixa, 2008, Suppl 1.
Byrn, Pharmaceutical Solids, a Strategic Approach to Regulatory Considerations, Pharmaceutical Research, 1995, vol. 12.
Morhenn (2), Keratinocyte proliferation in wound healing and skin diseases, Immunology Today, vol. 9, 1994.
Diabetes, Type 1 Diabetes-Associated Autoantibodies, 2009, vol. 52, Issue 8, p. 675-677.
Merck manual, 18th Edition, published Apr. 25, 2007, p. 594-598, Japanese Edition.
Scientific Discussion on Sifrol, EMEA, 2005, p. 1-9.
Scientific Discussion for Sifrol, European Public Assessment Reports, 2005, p. 1.
Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.
Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.
Hull, R. et al., "Nephrotic syndrome in adults." British Medical Journal, 2008, vol. 336, pp. 1185-1190.
Hunziker, D. et al, "Inhibitors of DPP IV-recent advances and structural views", Current Topics in Medicinal Chemistry, 2005, vol. 5 issue 16, pp. 1623-1637.
Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.
International Search Report—European Search Report for PCT/EP2003/09127 dated Mar. 1, 2011.
International Search Report and Written Opinion for PCT/EP2006/064657 dated Nov. 2, 2006.
International Search Report and Written Opinion for PCT/EP2007/054201 dated Aug. 29, 2007.
International Search Report and Written Opinion for PCT/EP2007/054270 dated Aug. 14, 2007.
International Search Report and Written Opinion for PCT/EP2008/060740 dated Mar. 30, 2009.
International Search Report and Written Opinion for PCT/EP2009/053978 dated Sep. 29, 2009.
International Search Report and Written Opinion for PCT/EP2009/056722 dated Aug. 13, 2009.
International Search Report and Written Opinion for PCT/EP2009/060521 dated Mar. 9, 2010.
International Search Report and Written Opinion for PCT/EP2009/063511 dated Feb. 26, 2010.
International Search Report and Written Opinion for PCT/EP2009/067772 dated Apr. 14, 2010.
International Search Report and Written Opinion for PCT/EP2010/050103 dated Mar. 22, 2010.
International Search Report and Written Opinion for PCT/EP2010/051093 dated Jul. 14, 2010.
International Search Report and Written Opinion for PCT/EP2010/051817 dated Jun. 8, 2010.
International Search Report and Written Opinion for PCT/EP2010/064691 dated Apr. 6, 2011.
International Search Report and Written Opinion for PCT/EP2010068349 dated Feb. 4, 2011.
International Search Report and Written Opinion for PCT/EP2011/054169 dated Aug. 4, 2011.
International Search Report and Written Opinion for PCT/EP2011/057163 dated Jun. 27, 2011.
International Search Report and Written Opinion for PCT/EP2011/057256 dated Jul. 22, 2011.
International Search Report and Written Opinion for PCT/EP2011/060449 dated Sep. 27, 2011.
International Search Report and Written Opinion for PCT/EP2011/070156 dated Jan. 17, 2012.
International Search Report and Written Opinion for PCT/EP2012/053910 dated May 14, 2012.
International Search Report and Written Opinion for PCT/EP2012/063852 dated Sep. 6, 2012.
International Search Report and Written Opinion for PCT/EP2012/077024 dated Feb. 19, 2013.
International Search Report and Written Opinion for PCT/EP2013/054524 dated Apr. 24, 2013.
International Search Report and Written Opinion for PCT/EP2013/059828 dated Aug. 6, 2013.
International Search Report and Written Opinion for PCT/EP2013/059831 dated Aug. 9, 2013.
International Search Report and Written Opinion for PCT/EP2013/060311 dated Aug. 9, 2013.
International Search Report and Written Opinion for PCT/EP2013/060312 dated Sep. 4, 2013.
International Search Report and Written Opinion for PCT/EP2013/070978 dated Oct. 31, 2013.
International Search Report and Written Opinion for PCT/EP2014/055113 dated May 16, 2014.
International Search Report and Written Opinion for PCT/EP2014/062398 dated Aug. 20, 2014.
International Search Report and Written Opinion for PCT/EP2015/054114 dated May 12, 2015.
International Search Report and Written Opinion for PCT/EP2015/074030 dated Feb. 4, 2016.
International Search Report and Written Opinon for PCT/EP2007/054204 dated Aug. 3, 2007.
International Search Report for PCT/EP03/12821 dated Mar. 30, 2004.
International Search Report for PCT/EP03/13648 dated Apr. 5, 2004.
International Search Report for PCT/EP2002/01820 dated May 7, 2002.
International Search Report for PCT/EP2003/12821 dated Mar. 30, 2004.
International Search Report for PCT/EP2003/13648 dated Apr. 5, 2004.

(56) References Cited

OTHER PUBLICATIONS

International Search Report for PCT/EP2005/001427 dated May 23, 2005.
International Search Report for PCT/EP2005/055711 dated Mar. 29, 2006.
International Search Report for PCT/EP2007/054204 dated Mar. 8, 2007.
International Search Report for PCT/EP2007/058181 dated Nov. 28, 2007.
International Search Report for PCT/EP2008/060738 dated Nov. 5, 2008.
International Search Report for PCT/EP2009/060170 dated Oct. 28, 2009.
The Textbook of Pharmaceutics, Pharmcaeutical Subcommitee Hanrimwon, 2005, p. 1-6.
Mettler Toledo "interpreting DSC curves Part 1: Dynamic Measurements" Jan. 2000. Available from www.masointechnology.ie.x/Usercom_11.pdf.
Glucophage (metformin hydrocholoride tablets) revised label, 2003.
Stahl, Selected Procedures for the Preparation of Pharmaceutically Acceptable salts, Handbook of Pharmaceutical Salts Properties, Chapter 11, 2015.
Caira, Crystalline Polymorphism of Organic Compounds, Topics in Current Chemistry, vol. 198, 2015.
Brittain, Polymorphism on Pharmaceutical Solids, Chapter 5 Generation of Polymorphs, vol. 95, 1999, p. 183-226.
Luo, Theory and Practice of Modern Physical Pharmacy, Shangai Scientific and Technical Literature Publishing House, 2005, p. 294.
Thomas, (R)-8-Amino-piperidin-1-yl)-7-but-2-ynyl-3-methyl-1-(4-methyl-quinazolin-2-ylmethyl)-3,7-dihydro-purine-2,6-dione(BI1236, a Novel Xanthine based Dipeptidyl Peptidase 4 inhibitor, has a Superior Potency and longer duration of action compared with other dipeptyl Peptidase-4 inhibitors, The Journal of Pharmacology and Experimental Therapeutica, vol. 325, 2008, p. 175-182.
Kim, Comparison of DPP-4 Inhibitors, The Journal of Korean Diabetes, http:dx.doi.org/10.4093/jkd.2013.14.3.111.
Medicine Department of Pharmacy, Pharmaceutical Subcommitte, Book Publishing Harwinton, 1996, p. 283.
Huang, et al. Elimination of metformin-croscarmellose sodium interaction by competition, International Journal of Pharmaceutics, 2006, p. 33-39.
Freeman, Initial Combination therapy for patients with type 2 diabetes mellitus, Drugs in Context, 2013, p. 212256.
Scheen, Efficacy and Safety of Jentadueto, Expert Opinion on Drug and Safety, vol. 12, No. 2, 2013, p. 275-289.
Haak, Initial Combination of linagliptin and metformin improves glycemic control in type 2 diabetes, Diabetes, Obesity and Metabolism, vol. 14, 2012, p. 565-574.
International Search Report and Written Opinion for PCT/EP2017/064007, dated Jun. 8, 2017.
Wikipedia, the free encyclopedia, The carbonyl group, 2017.
Controlling Temperature (Guidelines for the Storage of Essential Medicines and Other Health Commodities, 2003, http://apps.who.int.medicinedocs/en/d/Js4885e/6.5html).
Pharmaceutical Manufacturing and Storage (Concepts and Design, Inc.) 2009.
Methocel Cellulose Ethers in Aqueous Systems for tablet coating: retrieved from Internet: http://msdssearch.dow.com/PublishedLiteratureDOWCOM/dh_004a/0901b8038004ab56.pdf?filepath=198-00755.pd?fromPage=GetDoc, published2002. Retrieved Dec. 8, 2017.
Wu, Reactive Impurities in Excipients-Profiling, American Association of Pharmaceutical Scientists, 2011, vol. 12, No. 4, p. 1248-1263.
Waterman, Accelerating aging-Prediction of Chemical Stability of Pharmaceuticals, International Journal of Pharmaceutics, 2005, vol. 293, p. 101-125.
Herman, The DP-IV inhibitor MK-0431 enhances active GLP-1 and reduces Glucose following an OGTT in Type 2 Diabetics, American Diabetes Asociation, 2004.
Kaur, Development of new incretin drugs: Promising Therapies, Indian Journal Pharmacology, 2006, vol. 38, Issue 2, p. 100-106.
Clinical Trial results of Tradjenta Tablet, Center for Drug Evaluation and Research, 2010.
Pregelatinized Starch, Drugs.com, derived from https://drugs.com/inactive/pregelatinized-starch-136.html, accessed Nov. 17, 2017.
The textbooks of Pharmaceutics, Department of Pharmacy, Pharmaceutical Committee, 1996.
The Textbooks of Pharmaceutics, Department of Pharmacy, Pharmaceutical Subcommitee, 2000.
Approval material for Tradjenta tablet, Trial 1218.2, Center for Drug Eval. and Research, 2011.
Development Guideline for Excellent Drug, 2008, MFDS.
Doopedia, Maillard Reaction.
Hu, Diabetes Mellitus and Cardiovascular Disease, People's Military Medical Press, 2005, p. 211.
Susman,ADA: Linagliptin Works in Diabetic Kidney Disease, Med Page Today, 2011.
Announcement of the approval of Novel oral Diabetes Drug JANUVIA, Press Release, 2006.
Okano, Renal Clearance, New General Pharmaceutics, Revised 3rd Edition, 1987p. 213-215.
Clinical trials, a Randomized, Double Blind, Active Controlled parallel Group Efficacy and Safety Study of BI 1356 Compared to Glimepiride over 2 years in Type 2 Diabetic Patients with insufficient glycemic control despite metformin therapy, https://clinicaltrials.gov/archive/NCT00622284/20120606, 2008.
Eckhardt, "-(3-(R)-Aminopiperidin-1 -yl)7-but-2-ynyl-3-methyl-1-(4-methyl-quinazolin-2-ylmethyl-3,7-dihyd ropurine-2,6-dione (BI 1356), a highly potent, selective, long-acting, and orally bioavailable DPP-4 inhibitor for the treatment of type 2 diabetes", J. med. Chem, vol. 50, 2007.
Shigai, "How to use medicines in case of kidney injury caused by medicine" Journal of the Japanese Association of Rural Medicine, vol. 51, 2002, p. 63-67.
Zeng, "Efficacy and Safety of linagliptin added to metformin and sulphonylurea in Chinese patients with type 2 diabetes: a subanalysis of data from a randomised clinicial trial", Current Medical Research and Opinion, 2013.
Seino, Alogliptin plus voglibose in Japanese patients witrh type 2 diabetes: a randomized, double blind, placebo-controlled trial with an open label, long term extension, Current Medical Research and Opinion, 2011, vol. 27, p. 21-29.
Kurozumi, Efficacy of a-glucosidase inhibitors combined with dipeptylpeptidase-4 inhibitor for glucose fluctuation in patients with type 2 diabetes mellitus by continuous glucose monitoring, Journal of Diabetes Investigation, 2013, vol. 4, p. 393-398.
Horikawa, Synergistic Efffect of a-glucosidase inhibitors and dipeptidyl peptidase 4 inhibitor treatment, Journal of Diabetes Investigation, 2011, vol. 2, p. 200-203.
Yamazaki, Comparison of Efficacies of a Dipeptidyl Peptidase IV Inhibitor and a-Glucosodase Inhibitors in Oral Carbohydrate and Meal Tolerance Tests and their Effects of their tolerance in mice, J. Pharmacol Science, 2007, p. 29-38.
Kawamori, Linagliptin monotherapy provides superior glycaemic control v. placebo or voglibose with comparable safety in Japanese patients with type 2 diabetes, a randomized , placebo and active comparator-controlled doiuble blind study, 2011, Diabetes, Obesity and Metabolism, p. 348-357.
Inagaki, Linagliptin provides effective, well-tolerated add-on therapy to pre-existing oral antidiabetic therapy over 1 year in Japanese patients with type 2 diabetes, Diabetes, Obesity and Metabolis, 2013, p. 833-843.
Tang, Protection of DPP-4 inhibitors on cardiovascular, Drug Evaluation, vol. 9, 2012, p. 6-9.
Han, Basic and Clinical Coronary Heart Disease, Jilin Univ. Press, 2012, p. 114-118.
Lakey, Technical Aspects of Islet Preparation, Translp, Int.m 2003, vol. 16, p. 613-632.

(56) References Cited

OTHER PUBLICATIONS

White, Cardiovascular Events in patients receiving alogliptin, Diabetes Pro, 2010, vol. 59, p. 391.
Johansen, Cardiovascular safety with linagliptin on patients with type 2 diabetes mellitus, Cardiovascular Diabetology, 2012, vol. 11, p. 1-10.
Pham, New Onset Diabetes Mellitus After Solid Organ Transplantation, Endocrinology and Metabolism Clinics of North America, 2007, p. 873-890.
Ahren, Vascular Health and Risk Management, Novel combination treatment of type 2 diabetes DPP-4 inhibition plus metformin, 2008, p. 383-394.
Fuchs, Journal of Pharmacy and Pharmacology, Concentration-dependent plasma protein binding of the novel dipeptidyl peptidase 4 inhibitor BI 1356 due to saturable binding to its target in plasma of mice, rats and humans, 2009.
Linagliptin, Pub Chem, Clinical Trial Search of Japan, https;//pubchem.ncbi.nlm.nih.gov/compound/10096344 dated Jun. 25, 2020.
Ristic, Diabetes, Obesity and Metabolism, Improved Glycemic Control with dipeptidyl peptidase-4 inhibition in patients in patients with type 2 diabetes, 2005.
Aschner, Emerging Treatments and Technologies, Effect of the Dipepttidyl Peptidase-4 Inhibitor Sitagliptin as Monotherapy on Glycemic Control in Patients with Type 2 Diabetes, vol. 29, 2006.
Levien, Diabetes Spectrum, New Drugs in Development for the Treatment of Diabetes, vol. 22, 2009.
Mikhail, Incretin mimetics and dipeptidyl peptidase 4 inhibitors in clinical trials, expert Opinion on Investigational Drigs, 2008.
Huettner, Diabetes, Novel and Selective Xanthine, Jun. 2007 Supplement vol. 56.
Heizmann, Xanthines as scaffold for molecular diversity, Molecular doversity, vol. 2, 1996, p. 171-174.
Rabinovitch, Theophylline protects against diabetes in BB rats, Diabetologica, 1990.
De galan, Theophylline Improves Hypoglycemia Unawareness, Diabetes, vol. 51, 2002.
Mark, A novel and Selective Xanthine Based Competitive DPP-IV Inhibitor, Diabetes, vol. 56, 2007.
Abdoh, Amlodipine Besylate-Excipients Interaction in Solid Dosage Form, Phamra Dev. and Strategy, 2018.
Bruni, Drug Excipient Compatibility Studiesm J. of Thermal Analysis, 2018.
Crowley, Drug-Excipient interactions, Pharma Tech Europe, vol. 13, 2001.
Macdonald, No fraud, no conspiracy, no error, Pharmatechnologist, 2017.
Hanrinwon, Pharmaceutical Subcommittee, Pharmaceutics, p. 284-288, 1995.
Nathan, Managment of Hyperglycemia in Type 2 Diabetes, Diabetes Care, vol. 31, 2008.
Eckhardt, 8-)3-(R)-Aminopiperidin-l-yl)-7-but-2-ynyl-3-methyl-1-(4-methyl-quinazolin-2-ylmethyl)-3.7-dihyfropurine-2.6-dione (BI 1356), a highly potent, Selective, long-acting and Orally Bioavailable DPP-4 Inhibitor, J. Med Chem. vol. 50, 2007.
Forst, The novel, potent, and selective DPP-4 inhibitor, ADA Poster, 2007.
Heise, Pharmacokinetics, pharmacodynamics, and tolerablity of mutiple does of linagliptin, Diabetes, Obesity and Metabolism, vol. 11, 2009.
Schafer, Impaired glucagen like peptide 1 induced insulin secretions in carriers of transcription, Diabetologica, vol. 50, 2007.
Hu, Research and Application, Biomedical Info in Translational Research, 2008.
Pearson, Variation in TCF7L2Influences Therapeutic Response to Sulfonylreas, Diabetes, vol. 56, 2007.
Florez, Genetic Susteptibility to Type 2 Diabetes, J. of Diabetes, vol. 3, 2009.
Levien, New Drugs in Development for the Treatment of Diabetes, Diabetes Spectrum, vol. 22, 2009.
Graefe-Mody, Evaluation of the Potential for steady state phamracokinetic and pharmacodynamic interactions between the DPP-4 inhibitor linagliptin and metformin, Current Medical Research and Opinion, vol. 25, 2009.
Encyclopedia of Pharma Technology, Swarbrick, 3rd Ed., vol. 1, Absorption of Solid Surfaces, 2007.
Ahren, Emerging Dipeptyl peptidase-4 inhibitors for the treatment of diabetes, Expert Opinion on Emerging Drugs, vol. 13, 2008.
Ohlden, New data from Boehringer INgelheim's Ongoing Linagliptin Trial Programme Shows Promising Safety and Efficacy results, Newswire, 2020.
Lovshin, Incretin based therapies for type 2 diabetes mellitus, Nature, vol. 5, 2009.
Clinical Trials, NCT006002472, BI 1356 in combination with Metformin submitted Feb. 27, 2014.
Boehringer Ingelheim Press Release: Boehringer Ingelheim's diabetes Pipeline continues to advance as the company announces conclusion of robust Phase III pivotal trials programme for linalgiptin, Small Molecules, Published Sep. 28, 2009.
Wu, Primacy of the 3b Approach to Control risk factors for Cardiovascular dissease in type 2 diabetes patient,s Diabetes Mellitus and Cardio Disease, People's Military Press, 2005.
Diabetes and Foot Ulcers, www.diabetes.co.uk/diabetes-comolications/diabetic-foot-ulcers.html, 2018.
Nationale Versorgungs-Leitlinie, Diabetes Mellitus, 2004.
Deutsche Evidenzbasierte Diabetes-Leitlinien, Diabetes and Herz, 2002.
Menielly, Diabetes in Elderly adults, J. of Gerontolgy, vol. 56A, 2001.
Herrington, Metformin, Effective ans safe in renal Disease? Int. Urol. Nephrol. vol. 40, 2008.
Bruni, Drug Excipient compatibility, Journal of Thermal Analysis and Calorimetry, vol. 68, 2002.
Kibbe, Handbook of Pharmaceutical Excipients, 3rd Edition, 2009, p. 104-107.
Abdoh, Amlodipine besylate excipients interaction in solid dosage form, Pharmaceutical Development and Technology, vol. 9, 2004.
Crowley, Drug-Excipients Interactions, Pharmaceutical Technology Europe, vol. 13, 2001.
Wade, Organic Chem, 6th Edition, 2006, p. 918, 943-956.
News Article, https:/www.in-phamratechnologist.com-Article-France-and-maerck-say-reformulated-Euthyrox-is-safe.)—Sep. 17, 2017.
Hu, Diabetes Mellitus and Heart Disease, People's Military Press, 2005.
Nursten, The Mailard Reaction, Chemistry, Biochemistry, and Implications, Chapter 10, p. 1-8., 2018.
DiFeo, Drug Product Development, A Technical Review of Chemistry, Drug Development and Industrial Pharmacy, vol. 29, 2003, p. 939-958.
Federal register, Department of Health and Human Services, vol. 62, 1997.
Van Veen, Compaction of Powder blends, University Medical Center, 2003.
MacDonald, No Fraud, no conspiracy, no error, France and Merck say reformulated Euthyrox is safe, Pharmatechnolgist, 2017.
Nachaegari, Coprocessed Excipients for Solid Dosage Forms, Pharmaceutical technology, 2004.
Gohel, A review of coprocessed Directly compressible excipients, J. Pharm Pharmaceutical Sci, 2005.
Cotton, The Selection of an appropriate salt form and preparation of a stable oral formulation, International Journal of Pharmaceutics, 1994, p. 237-249.
Ahmed, Materials Formulation of Low Dose Medicines, Americal Pharma review, vol. 3, 2000.
Wikipedia, Polyvinylpyrrolidone, https:en.wikipedia.org/wiki/ access date May 15, 2018.
Westerhuis, Optimisation of the composition and production of mannitol cellulose tablets International Journal of Pharmaceutics, 1996, p. 143, 151-162.
Portincasa, Current Pharmacological Treatment of Nonalcoholic Fatty Liver, Current Medicinal Chem, 2006, p. 2889-2900.
Del Prato, Diabetes, Obesity and Metabolism, Effect of linagliptin monotherapy on glycemic control and markers of b-cell function in

(56) References Cited

OTHER PUBLICATIONS patients with inadequately controlled type 2 diabetes: a randomized controlled trial, 2011, p. 258-267.
Gallwitz, linagliptin—A novel Dipeptidyl Peptidase Inhibitor for Type 2 Diabetes Therapy, Clinical Medicine Indights: Endocrinology and Diabetes, 2012, vol. 5, p. 1-11.
Lakey, Technical Aspects of islet preparation and transplantation, Burridge Medical Researach Institute, 2003.
Mikhail, Investigating Drugs, Incretin Mimetics and dipeptidyl peptidase 4 inhibitors in clinical trials for the treatment of Type 2 diabetes, vol. 17, 2008, p. 845-853.
Cefalu, Animal Models of Type 2 Diabetes: Clinical Presentation and Pathophysiological Relevance to the Human Condition, ILAR Journal, vol. 47, No. 3, 2006.
Crowe, Early Guidelines and Identification Management of Chronic Kidney Disease, 2008, summary of NICE guidance, vol. 337, p. 812-815.
Zaman, Comparison Between Effect of Vildagliptin and Linagliptin on Glycaemic control, renal function, liver funstion and lipid profile in patients of T2DM Inadequately controlled with combo of Metformin and Glimepiride, Journal of Dental and Medical Sciences, vol. 16, Issue 9, 2017. p. 27-31.
Connelly, Dipeptyl peptidase-4 inhibition improves left ventricular function in chronic kidney disease, Clinical and Investigative Medicine, vol. 37, p. 172-185, 2014.
Scheen, Clinical Pharmacokinetics of metformin, Clinical Pharmacokinetics, vol. 30, No. 5, 1996, p. 359-371.
Zhang, Classification and Treatment Priniciples of Diabetes, Beijing Medical Univ and China Union Medical Univ. Joint Publishing House. 1st ed., 1998, p. 389.
Diabetes and Foot ulcers, www.diabetes.co.uk/diabetes-complications/diabetic-foot-ulcers.html, 2018.
Aronow, Congestive Heart Failure, Treatment of Heart Failure in Older Persons with Coexisting Conditions, vol. 9, No. 3, 2003, p. 142-147.
Tiwari, Linagliptin, A dipeptyl peptidase-4 inhibitor for the treatment of type 2 diabetes, Current Opinion in Ivestigational Drugs, vol. 10, 2009, p. 1091-1104.
Isomaa, Chronic Comlications in patients with slowly progressing atutoimmune type 1 diabetes, Diabetes Care, vol. 22, 1999, p. 1347-1353.
Seijin-byou, The Journal of Adult Diseases, 2008, vol. 38, p. 438-444., abstract attached.
Fuguchi, Therapeutic Effects and Adverse Reactions to Oral Hypoglycemic Agents, Journal of the Nippon Hospital Pharmacists Assoc, 1976, vol. 1, p. 226-229, abstract only.
Colorcon (retrieved from website http://www.colorcon.com/products-formulation/all-products/film-coatings/immediate-release/opadry, published2015).
Bergmann, Decrease of serum dipeptidylpeptidase activity in severs sepsis patients, Clinica Chimica Acta 2002., p. 123-126.
Gallwitz, Safety and Efficacy of linagliptin in type 2 diabetes patients with common renal and cardiovascular risk factors, vol. 4,2013.
Groop, Effects of the DPP-4inhibitor linagliptin on albuminuria in patients with type 2 diabetes, www.abstractsonline.com, 2013.
Cooper, Kidney Disease End Points in a Pooled Analysis of individual Patient-Level Data from a large Clinical Trials Program of the Dipeptyl Peptidase 4 Inhibitor Linagliptin in Type 2 Diabetes, vol. 66, American Journal of Kidney Diseases, 2015.
Hocher, Renal and Cardiac Effects of DPP4 in inhibitors from preclinical development to clinical research, Kidney and Blood Pressure Research, vol. 36, 2012, p. 65-84.
Von Eynatten, Efficacy and safety of linagliptin in type 2 diabetes subjects at high risk for renal and cardiovascular disease, vol. 12, 2013.
Seijin-byou, abstract, The Journal of Adult Diseases, 2008. , vol. 38. Clinical Journal of Chinese Medicine, vol. 3, 2008, p. 360-364.
Clinical Trials.gov, Efficacy and Safety of Lingliptin in Elderly Patients with Type 2 Diabetes, Mar. 10, 2010, NCT01084005.
Barrara, Granulation, Handbook of Powder Technology, vol. 11, 2015.
Piatti, Long term Oral L-Arginine-Administration Improves Peripheral and Hepatic Insulin Sensitivity, Emerging Treatments and Technology, Diabestes Care, vol. 24, 2011.
Clinical Trials.gov, NCT00622284, Efficacy and Safety of BI 1356 in Combination with Metformin in Patients with Type 2 Diabetes, 2013.
Kleeman, Pharmaceutical Substances, Synthesesm Patents, Applications, p. 1196-1997, 1999.
Rowe, Handbook of Pharmaceutical Excipients, Fifth Ed., Calcium Bicarbonate, 2006.
Clinical Trials.gov, Efficacy and Safety of BI 1356 in Combination with Metformin in Patients with Type 2 Diabetes, NCT00309608, 2006.
Clinical Trials.gov, 52-week add-on to metformin comparison of saxagliptin and sulphonurea, NCT00575588, 2007.
Walsh, Pharmaceutical Biotechnology,Ovewview of Protein structure, 2007.
Katdare, Excipient Development for Pharmaceutical Biotechnology and Drug Delivery Systems, Ten of the most common Neutralizers Used, 2006.
Remington , The Science of Pharmacy, 22nd Ed., Pharmacuetical Dosage Forms, 2013.
Lide, CRC Handbook of Chem and Physics, Disassociation Constants of Organic Acids and Bases, 2002, 82nd Ed.
Stahl, Handbook of Pharmaceutical Salts, Properties, Selection and Use, 2002.

* cited by examiner

POLYMORPHS

BACKGROUND OF THE INVENTION

This Application claims priority of EP 06 009 202, which is hereby incorporated by reference in its entirety.

1. Field of the Invention

The invention relates to polymorphous crystal modifications of a DPP-IV inhibitor, the preparation thereof and the use thereof for preparing a medicament.

2. Description of the Prior Art

The enzyme DPP-IV, also known by the name CD26, is a serine protease which promotes the cleaving of dipeptides in proteins with a proline or alanine group at the N-terminal end. DPP-IV inhibitors thereby influence the plasma level of bioactive peptides including the peptide GLP-1. Compounds of this type are useful for the prevention or treatment of illnesses or conditions which are associated with an increased DPP-IV activity or which can be prevented or alleviated by reducing the DPP-IV activity, particularly type I or type II diabetes mellitus, prediabetes, or reduced glucose tolerance.

WO 2004/018468 describes DPP-IV inhibitors with valuable pharmacological properties. One example of the inhibitors disclosed therein is 1-[(4-methyl-quinazolin-2-yl)methyl]-3-methyl-7-(2-butyn-1-yl)-8-(3-(R)-amino-piperidin-1-yl)-xanthine.

DETAILED DESCRIPTION OF THE INVENTION

Figure 1:
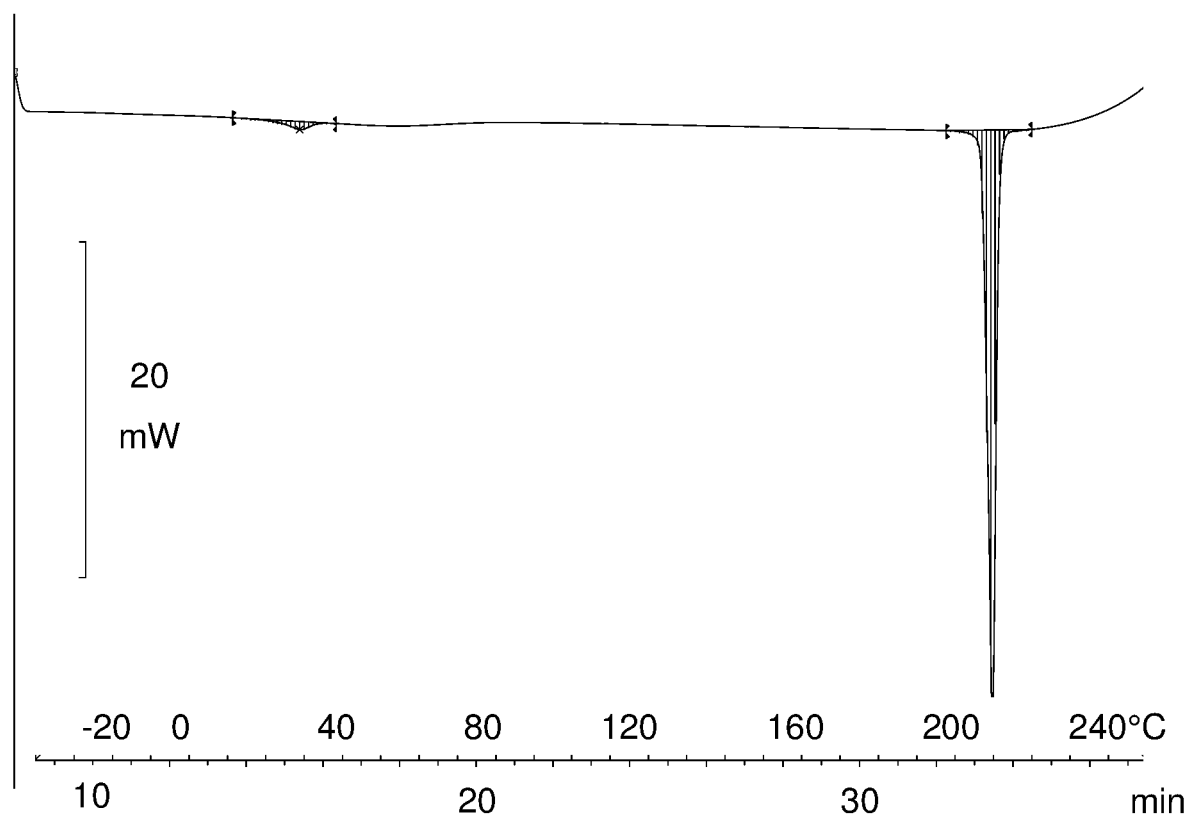
FIG. 1 shows the thermoanalysis of the anhydrous form A/B.

Within the scope of the present invention it has been found that 1-[(4-methyl-quinazolin-2-yl)methyl]-3-methyl-7-(2-butyn-1-yl)-8-(3-(R)-amino-piperidin-1-yl)-xanthine may take on various polymorphous crystal modifications and that the compound prepared in WO 2004/018468 is present at ambient temperature as a mixture of two enantiotropic polymorphs. The temperature at which the two polymorphs transform into one another is 25±15° C. (see FIGS. 1 and 2).

The pure high temperature form (polymorph A), which can be obtained by heating the mixture to temperatures >40° C., melts at 206±3° C. In the X-ray powder diagram (see FIG. 3) this form shows characteristic reflections at the following d values: 11.49 Å, 7.60 Å, 7.15 Å, 3.86 Å, 3.54 Å and 3.47 Å (cf. also Table 1 and 2).

Anhydrous polymorph A may be prepared by
(a) refluxing 1-[(4-methyl-quinazolin-2-yl)methyl]-3-methyl-7-(2-butyn-1-yl)-8-(3-(R)-amino-piperidin-1-yl)-xanthine in absolute ethanol and optionally filtering the mixture,
(b) cooling the hot solution or the hot filtrate until crystallisation sets in,
(c) diluting with a solvent such as tert.-butylmethylether,
(d) suction filtering the solvent mixture and
(e) drying the polymorph A at 45° C. in vacuo.

The low temperature form (polymorph B) is obtained by cooling to temperatures <10° C. In the X-ray powder diagram (see FIG. 4) this form shows characteristic reflections at the following d values: 11.25 Å, 9.32 Å, 7.46 Å, 6.98 Å and 3.77 Å (cf. also Table 3 and 4).

Anhydrous polymorph B may be prepared by
(a) dissolving 1-[(4-methyl-quinazolin-2-yl)methyl]-3-methyl-7-(2-butyn-1-yl)-8-(3-(R)-amino-piperidin-1-yl)-xanthine in absolute ethanol and refluxing and optionally filtering the mixture,
(b) cooling the hot solution or the hot filtrate for crystallisation to a temperature below 10° C.,
(c) diluting with a solvent such as tert.-butylmethylether,
(d) suction filtering the solvent mixture and
(e) drying the polymorph at a temperature below 10° C. in vacuo.

Another polymorph (polymorph C) shows characteristic reflections in the X-ray powder diagram (see FIG. 5) at the following d values: 12.90 Å, 11.10 Å, 6.44 Å, 3.93 Å and 3.74 Å (cf. also Table 5).

Polymorph C is obtained if
(a) 1-[(4-methyl-quinazolin-2-yl)methyl]-3-methyl-7-(2-butyn-1-yl)-8-(3-(R)-amino-piperidin-1-yl)-xanthine is dissolved in methanol and refluxed and optionally filtered in the presence of activated charcoal,
(b) the methanolic solution is cooled to a temperature of 40-60° C.,
(c) a solvent such as tert.-butylmethylether or diisopropylether is added,
(d) the resulting suspension is first of all cooled slowly to 15-25° C. and then later to 0-5° C.,
(e) the crystals formed are suction filtered and washed again with tert.-butylmethylether or diisopropylether and
(f) the crystals thus obtained are dried at a temperature of 70° C. in the vacuum dryer.

Another polymorph (polymorph D) melts at 150±3° C. This polymorph is obtained if polymorph C is heated to a temperature of 30-100° C. or dried at this temperature.

Finally, there is also polymorph E, which melts at a temperature of 175±3° C. Anhydrous polymorph E is formed if polymorph D is melted. On further heating, polymorph E crystallises out of the melt.

The polymorphs thus obtained may be used in the same way as the mixture of the two polymorphs A and B described in WO 2004/018468 for preparing a pharmaceutical composition which is suitable for treating patients with type I and type II diabetes mellitus, prediabetes or reduced glucose tolerance, with rheumatoid arthritis, obesity, or calcitonin-induced osteoporosis, as well as patients in whom an allograft transplant has been carried out. These medicaments contain in addition to one or more inert carriers at least 0.1% to 0.5%, preferably at least 0.5% to 1.5% and particularly preferably at least 1% to 3% of one of the polymorphs A, B, or C.

The following Examples are intended to illustrate the invention in more detail.

EXAMPLE 1

Crystallisation of Polymorph A

Crude 1-[(4-methyl-quinazolin-2-yl)methyl]-3-methyl-7-(2-butyn-1-yl)-8-(3-(R)-amino-piperidin-1-yl)-xanthine is refluxed with 5 times as much absolute ethanol and the hot solution is filtered clear through activated charcoal. After the filtrate has been cooled to 20° C. and crystallisation has set in, the solution is diluted to double the volume with tert.-butylmethylether. Then the suspension is cooled to 2° C., stirred for 2 hours, suction filtered and dried in the vacuum dryer at 45° C.

FIG. 1 shows the thermoanalysis of the anhydrous form A/B.

Polymorph A melts at 206±3° C. In the DSC diagram another slightly endothermic signal can be seen at approx. 25° C. This is a fully reversible solid-solid phase transition between the two enantiotropic crystal modifications A and B. The form A is the thermodynamically stable modification above this transformation temperature, w| form B is the thermodynamically stable modification below this transformation temperature.

Figure 2:
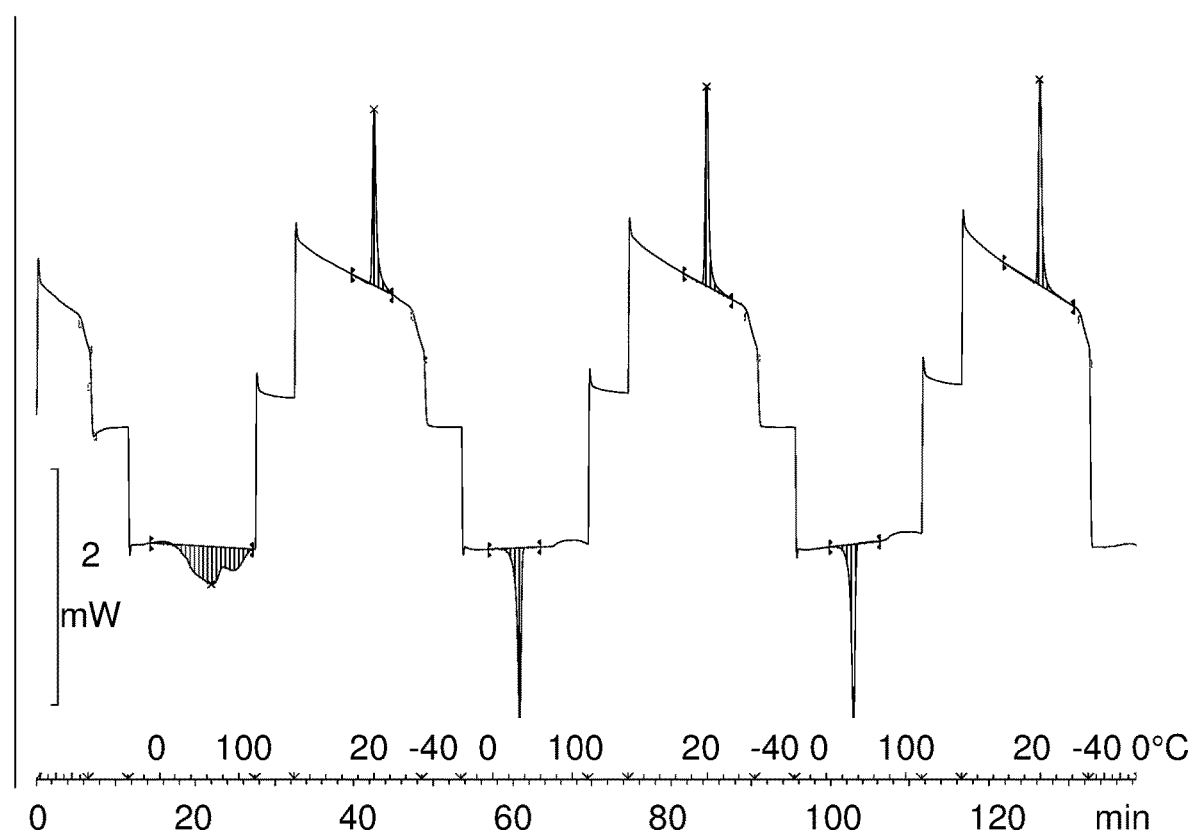
FIG. 2 shows a cyclic DSC diagram, in which the phase transition from −40° C. to 120° C. and vice versa has been run through a total of 3 times.

FIG. 2 shows a cyclic DSC diagram, in which the phase transition from −40° C. to 120° C. and vice versa has been run through a total of 3 times. During heating, the phase transition is observed as an endothermic signal and, correspondingly, during cooling it is observed as an exothermic signal. During the first heating cycle the phase transition may also be observed as an endothermic double signal or as a very broad signal while in all the other cycles the signal occurs as a very sharp endothermic or exothermic signal, depending on whether heating or cooling is taking place.

Figure 3:
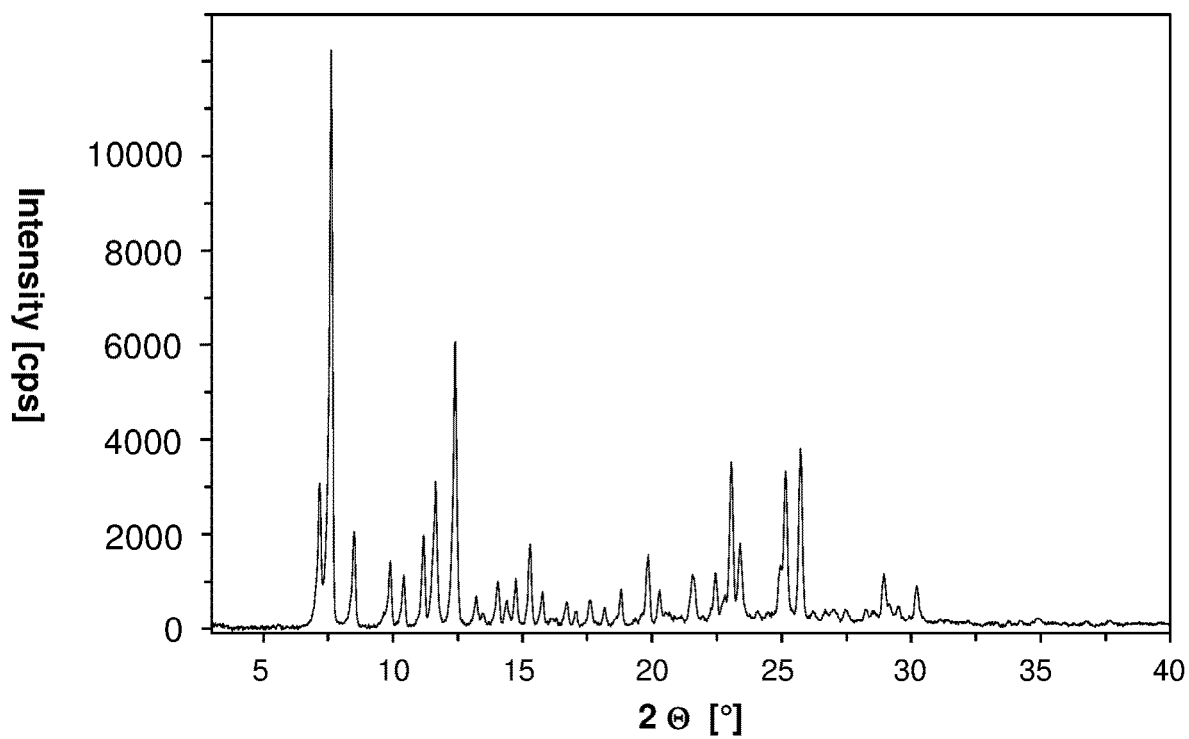
FIG. 3 shows an X-ray powder diagram of the anhydrous form A.

FIG. 3 shows an X-ray powder diagram of the anhydrous form A

TABLE 1

Labelled X-ray reflections up to 30° 2 Θ with intensities (standardised) for the anhydrous polymorph A

| 2 Θ | intensity | $d_{hkl}$ | labelling | | | $d_{exp-calc}$ |
|---|---|---|---|---|---|---|
| [°] | I/I$_o$ [%] | [Å] | h | k | l | [Å] |
| 5.56 | 1 | 15.89 | 1 | 0 | 0 | −0.008 |
| 7.18 | 32 | 12.31 | 0 | 1 | 1 | 0.005 |
| 7.62 | 100 | 11.59 | 1 | 1 | 0 | 0.007 |
| 8.49 | 20 | 10.41 | −1 | 1 | 1 | 0.002 |
| 9.91 | 24 | 8.92 | 0 | 0 | 2 | 0.003 |
| 10.41 | 18 | 8.49 | 0 | 2 | 0 | 0.024 |
| 11.18 | 24 | 7.91 | 2 | 0 | 0 | 0.038 |
| 11.63 | 41 | 7.60 | −1 | 1 | 2 | 0.003 |
| 12.37 | 59 | 7.15 | −1 | 2 | 1 | −0.003 |
| 13.19 | 6 | 6.71 | 1 | 2 | 1 | −0.014 |
| 13.45 | 3 | 6.58 | −2 | 0 | 2 | 0.007 |
| 14.05 | 6 | 6.30 | 2 | 1 | 1 | 0.011 |
| 14.38 | 6 | 6.16 | 0 | 2 | 2 | 0.003 |
| 14.71 | 10 | 6.02 | −1 | 2 | 2 | −0.008 |
| 15.26 | 13 | 5.80 | 2 | 2 | 0 | 0.001 |
| 15.76 | 10 | 5.62 | −1 | 1 | 3 | 0.008 |
| 16.09 | 1 | 5.51 | 1 | 2 | 2 | −0.010 |
| 16.32 | 1 | 5.43 | 2 | 0 | 2 | 0.035 |
| 16.69 | 4 | 5.31 | 2 | 2 | 1 | −0.007 |
| 17.03 | 3 | 5.20 | −1 | 3 | 1 | 0.026 |
| 17.63 | 6 | 5.03 | 1 | 3 | 1 | 0.006 |
| 18.17 | 5 | 4.88 | −1 | 2 | 3 | −0.004 |
| 18.78 | 7 | 4.72 | −1 | 3 | 2 | −0.014 |
| 19.30 | 1 | 4.60 | −2 | 3 | 1 | −0.019 |
| 19.61 | 2 | 4.52 | −3 | 2 | 1 | 0.036 |
| 19.86 | 20 | 4.47 | −2 | 2 | 3 | 0.040 |
| 20.29 | 10 | 4.37 | 2 | 0 | 3 | 0.019 |
| 20.57 | 4 | 4.31 | 0 | 1 | 4 | 0.006 |
| 21.12 | 1 | 4.20 | 3 | 0 | 2 | 0.048 |
| 21.57 | 12 | 4.12 | −2 | 1 | 4 | 0.028 |
| 22.46 | 10 | 3.96 | 1 | 4 | 1 | 0.035 |
| 23.03 | 35 | 3.86 | 4 | 1 | 0 | 0.022 |
| 23.39 | 21 | 3.80 | −1 | 4 | 2 | 0.019 |
| 24.08 | 2 | 3.69 | −3 | 1 | 4 | −0.006 |
| 24.51 | 1 | 3.63 | −4 | 0 | 3 | 0.036 |
| 24.91 | 10 | 3.57 | −2 | 4 | 2 | 0.003 |
| 25.14 | 39 | 3.54 | 3 | 1 | 3 | 0.043 |
| 25.69 | 36 | 3.47 | −3 | 3 | 3 | 0.041 |
| 26.68 | 3 | 3.34 | 0 | 5 | 1 | 0.035 |
| 26.90 | 2 | 3.31 | 3 | 4 | 0 | 0.027 |
| 27.10 | 2 | 3.29 | 0 | 2 | 5 | 0.030 |
| 27.42 | 3 | 3.25 | 4 | 3 | 0 | 0.006 |
| 28.19 | 2 | 3.16 | −1 | 5 | 2 | −0.035 |
| 28.54 | 2 | 3.12 | 3 | 0 | 4 | 0.047 |
| 28.94 | 11 | 3.08 | 0 | 4 | 4 | −0.036 |
| 29.18 | 5 | 3.06 | −4 | 3 | 3 | 0.017 |
| 29.50 | 4 | 3.03 | −1 | 0 | 6 | 0.041 |
| 30.18 | 7 | 2.96 | −1 | 5 | 3 | −0.042 |

TABLE 2

Lattice metrics of the anhydrous form A

| Symmetry: | monoclinic |
|---|---|
| space group: | P |
| a: | 16.16(2) Å |
| b: | 17.02(1) Å |
| c: | 18.18(2) Å |
| β: | 100.95(6)° |
| cell volume: | 4907(11) Å³ |

EXAMPLE 2

Crystallisation of Polymorph B

Polymorph B is obtained by cooling form A from Example 1 to temperatures <10° C.

Figure 4:
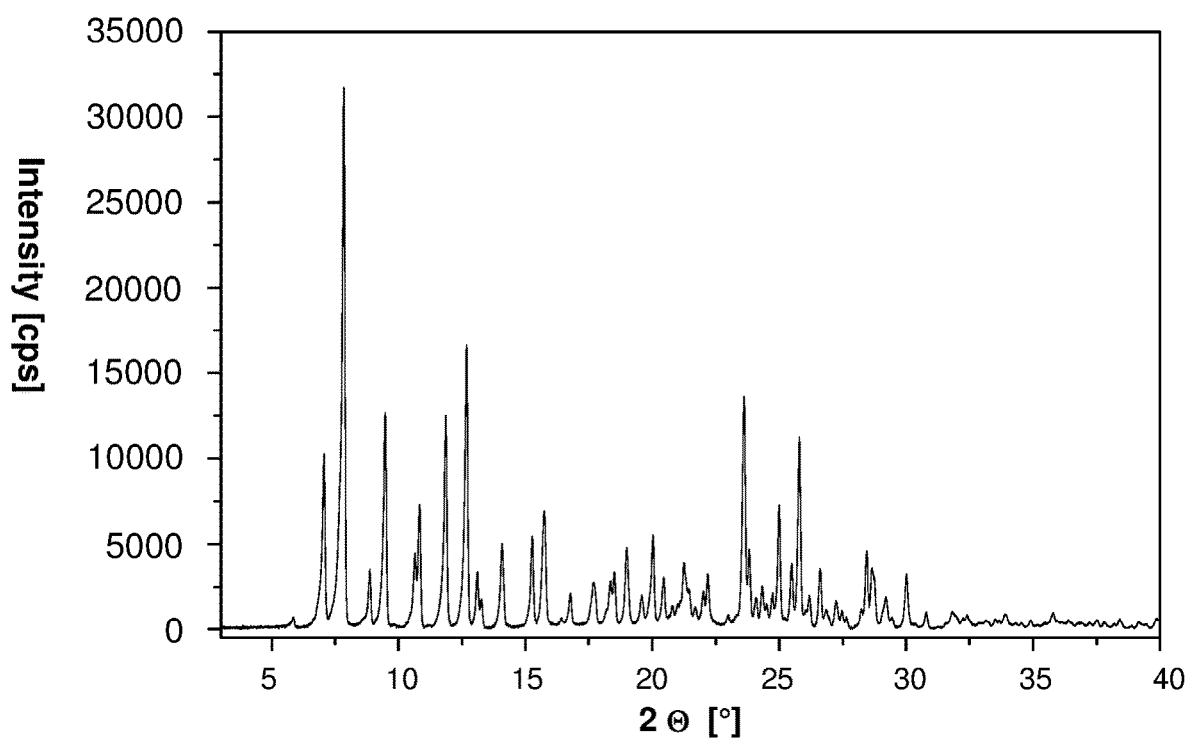
FIG. 4 shows an X-ray powder diagram of the anhydrous form B.

FIG. 4 shows an X-ray powder diagram of the anhydrous form B

TABLE 3

Labelled X-ray reflections up to 30° 2 Θ with intensities (standardised) for the anhydrous form B

| 2 Θ | intensity | $d_{hkl}$ | labelling | | | $d_{exp-calc}$ |
|---|---|---|---|---|---|---|
| [°] | I/I$_o$ [%] | [Å] | h | k | l | [Å] |
| 5.82 | 3 | 15.17 | 1 | 0 | 0 | −0.007 |
| 7.04 | 33 | 12.55 | 0 | 1 | 1 | 0.001 |
| 7.82 | 100 | 11.3 | 1 | 1 | 0 | −0.004 |
| 8.84 | 11 | 10 | −1 | 1 | 1 | 0.001 |
| 9.44 | 40 | 9.36 | 1 | 1 | 1 | 0.011 |
| 10.62 | 14 | 8.32 | −1 | 0 | 2 | 0.013 |
| 10.79 | 24 | 8.19 | 0 | 1 | 2 | −0.005 |
| 11.82 | 39 | 7.48 | −1 | 1 | 2 | −0.003 |
| 12.64 | 53 | 7 | −1 | 2 | 1 | −0.009 |
| 13.07 | 11 | 6.77 | 1 | 2 | 1 | −0.006 |
| 13.24 | 6 | 6.68 | −2 | 1 | 1 | 0.004 |
| 14.04 | 16 | 6.3 | 2 | 1 | 1 | 0.003 |
| 15.23 | 17 | 5.81 | −2 | 1 | 2 | 0.003 |
| 15.70 | 22 | 5.64 | 2 | 2 | 0 | 0.016 |
| 16.38 | 2 | 5.41 | 0 | 3 | 1 | −0.010 |

TABLE 3-continued

Labelled X-ray reflections up to 30° 2 Θ with intensities (standardised) for the anhydrous form B

| 2 Θ [°] | intensity I/I$_o$ [%] | d$_{hkl}$ [Å] | h | k | l | d$_{exp-calc}$ [Å] |
|---|---|---|---|---|---|---|
| 16.73 | 6 | 5.3 | 2 | 2 | 1 | 0.008 |
| 17.67 | 8 | 5.02 | 0 | 2 | 3 | 0.014 |
| 18.16 | 3 | 4.88 | −1 | 2 | 3 | 0.005 |
| 18.33 | 9 | 4.84 | 3 | 1 | 0 | 0.016 |
| 18.48 | 10 | 4.8 | −3 | 1 | 1 | −0.003 |
| 18.97 | 15 | 4.68 | 0 | 0 | 4 | −0.001 |
| 19.56 | 6 | 4.54 | 1 | 3 | 2 | 0.013 |
| 20.00 | 17 | 4.44 | 2 | 1 | 3 | 0.000 |
| 20.42 | 9 | 4.35 | 1 | 0 | 4 | 0.009 |
| 20.76 | 4 | 4.27 | 3 | 0 | 2 | −0.014 |
| 20.97 | 4 | 4.23 | 0 | 4 | 0 | 0.010 |
| 21.07 | 5 | 4.21 | 1 | 1 | 4 | −0.009 |
| 21.22 | 12 | 4.18 | 0 | 3 | 3 | 0.001 |
| 21.40 | 7 | 4.15 | 3 | 2 | 1 | 0.004 |
| 21.66 | 4 | 4.1 | −1 | 3 | 3 | 0.018 |
| 21.98 | 7 | 4.04 | 2 | 2 | 3 | −0.003 |
| 22.16 | 10 | 4.01 | −3 | 1 | 3 | 0.008 |
| 22.97 | 3 | 3.87 | 1 | 2 | 4 | −0.006 |
| 23.58 | 43 | 3.77 | −2 | 3 | 3 | −0.003 |
| 23.78 | 15 | 3.74 | −2 | 2 | 4 | −0.004 |
| 24.05 | 6 | 3.7 | 4 | 1 | 0 | −0.002 |
| 24.29 | 8 | 3.66 | −2 | 4 | 1 | −0.008 |
| 24.46 | 5 | 3.64 | 3 | 3 | 1 | 0.018 |
| 24.71 | 7 | 3.6 | 0 | 3 | 4 | 0.001 |
| 24.96 | 23 | 3.56 | 2 | 3 | 3 | −0.001 |
| 25.45 | 12 | 3.5 | −2 | 4 | 2 | −0.010 |
| 25.75 | 35 | 3.46 | 4 | 2 | 0 | 0.011 |
| 25.99 | 4 | 3.43 | 3 | 2 | 3 | 0.014 |
| 26.15 | 6 | 3.41 | 3 | 3 | 2 | 0.010 |
| 26.57 | 12 | 3.35 | −2 | 3 | 4 | −0.001 |
| 26.82 | 4 | 3.32 | −3 | 2 | 4 | 0.011 |
| 27.20 | 6 | 3.28 | 1 | 2 | 5 | −0.010 |
| 27.43 | 4 | 3.25 | −2 | 4 | 3 | −0.003 |
| 27.60 | 3 | 3.23 | −2 | 2 | 5 | −0.005 |
| 28.19 | 4 | 3.16 | 3 | 4 | 1 | 0.010 |
| 28.40 | 15 | 3.14 | 0 | 4 | 4 | −0.013 |
| 28.64 | 12 | 3.11 | 0 | 0 | 6 | 0.016 |
| 29.18 | 6 | 3.06 | −4 | 3 | 2 | 0.004 |
| 29.42 | 2 | 3.03 | 1 | 4 | 4 | 0.002 |
| 29.99 | 10 | 2.98 | 0 | 5 | 3 | −0.008 |
| 30.77 | 3 | 2.9 | −4 | 3 | 3 | 0.018 |

TABLE 4

Lattice metrics of the anhydrous form B

| Symmetry: | monoclinic |
|---|---|
| space group: | P2$_1$/c (# 14) |
| a: | 15.23(1) Å |
| b: | 16.94(1) Å |
| c: | 18.79(1) Å |
| β: | 95.6(2)° |
| cell volume: | 4823(3) Å$^3$ |

EXAMPLE 3

Crystallisation of Polymorph C

Crude 1-[(4-methyl-quinazolin-2-yl)methyl]-3-methyl-7-(2-butyn-1-yl)-8-(3-(R)-amino-piperidin-1-yl)-xanthine (26 kg) is refluxed with 157 l methanol, combined with 1.3 kg of activated charcoal and after 30 minutes' stirring the mixture is filtered and rinsed with 26 l methanol. 122 l of methanol are distilled off from the filtrate, then the residue is cooled to 45-55° C. 52 l of tert.-butylmethylether are added to the residue over 30 minutes. Then the mixture is stirred for another 60 minutes at 45-55° C. Crystallisation takes place within this time. A further 78 l tert. butylmethylether are added to the suspension over 30 minutes and then it is stirred again for a further 60 minutes at 45-55° C. It is diluted to four times the volume. The suspension is slowly cooled to 15-25° C. and stirred overnight at this temperature. After the suspension has been cooled to 0-5° C. the crystals are suction filtered, washed with 2 batches tert.-butylmethylether and dried at 70° C. in the vacuum dryer.

Figure 5:
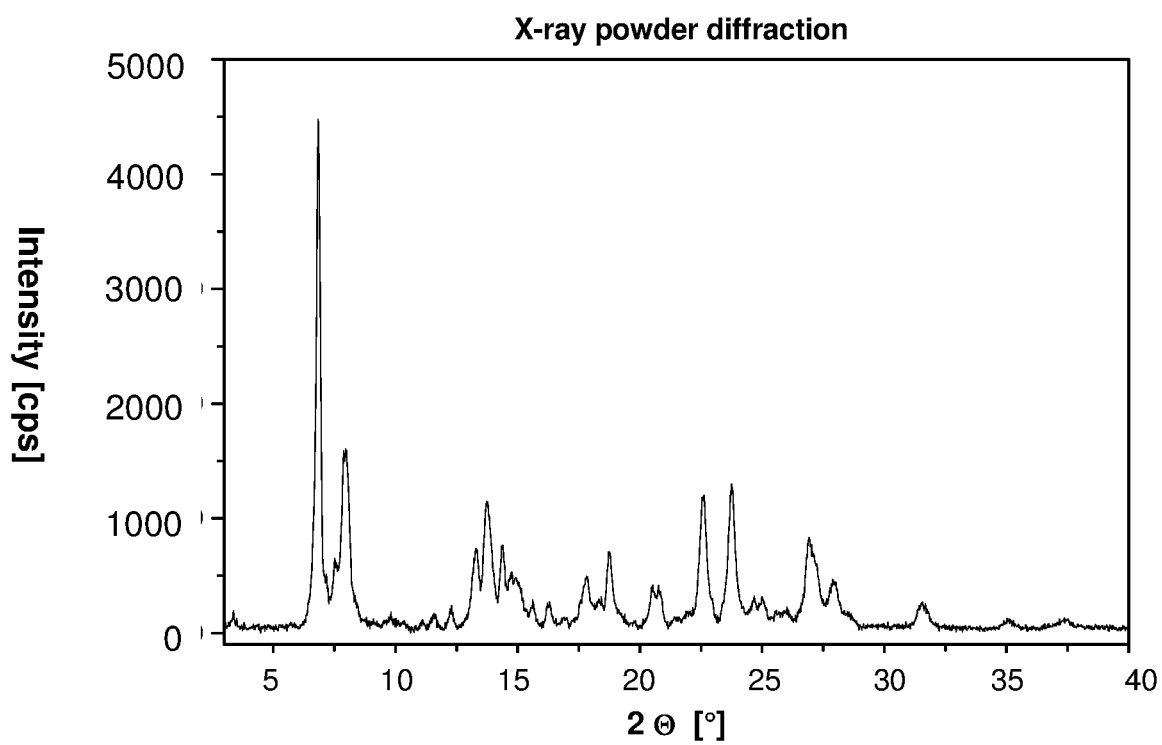
FIG. 5 shows an X-ray powder diagram of polymorph C.

FIG. 5 shows an X-ray powder diagram of polymorph C

TABLE 5

X-ray reflections up to 30° 2 Θ with intensities (standardised) for the anhydrous form C

| 2 Θ [°] | d$_{hkl}$ [Å] | intensity I/I$_o$ [%] |
|---|---|---|
| 3.38 | 26.16 | 4 |
| 6.85 | 12.90 | 100 |
| 7.18 | 12.31 | 11 |
| 7.52 | 11.74 | 14 |
| 7.96 | 11.10 | 36 |
| 9.80 | 9.02 | 3 |
| 11.11 | 7.96 | 2 |
| 11.58 | 7.64 | 3 |
| 12.30 | 7.19 | 5 |
| 13.30 | 6.65 | 16 |
| 13.75 | 6.44 | 26 |
| 14.38 | 6.16 | 17 |
| 14.74 | 6.01 | 11 |
| 14.95 | 5.92 | 10 |
| 15.63 | 5.66 | 6 |
| 16.28 | 5.44 | 5 |
| 17.81 | 4.98 | 10 |
| 18.33 | 4.83 | 6 |
| 18.75 | 4.73 | 15 |
| 20.51 | 4.33 | 8 |
| 20.77 | 4.27 | 8 |
| 21.47 | 4.14 | 3 |
| 21.96 | 4.05 | 4 |
| 22.59 | 3.93 | 26 |
| 23.76 | 3.74 | 29 |
| 24.68 | 3.60 | 6 |
| 25.01 | 3.56 | 7 |
| 25.57 | 3.48 | 4 |
| 25.96 | 3.43 | 4 |
| 26.93 | 3.31 | 18 |
| 27.22 | 3.27 | 13 |
| 27.92 | 3.19 | 10 |

EXAMPLE 4

Crystallisation of Polymorph D

Polymorph D is obtained if polymorph C from Example 3 is heated to a temperature of 30-100° C. or dried at this temperature.

EXAMPLE 5

Crystallisation of Polymorph E

Anhydrous polymorph E is obtained if polymorph D is melted. On further heating, polymorph E crystallises out of the melt.

Figure 6:
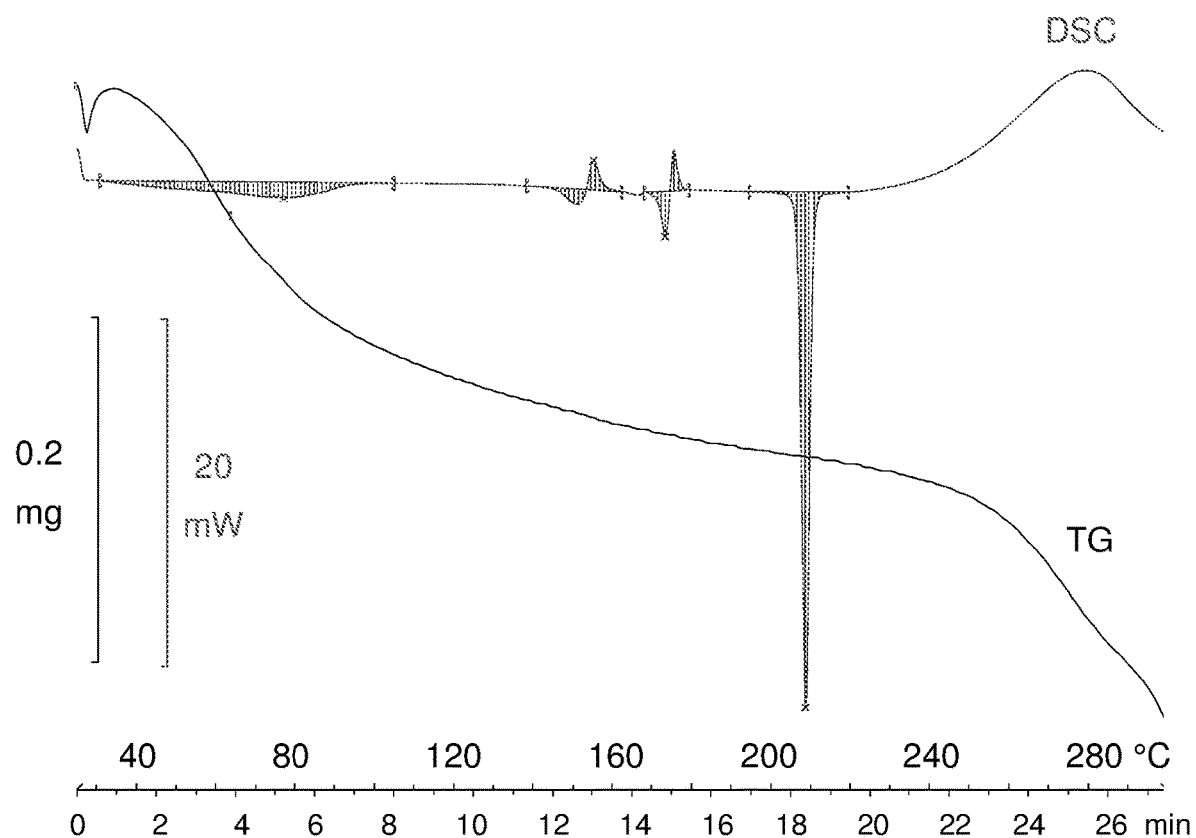
FIG. 6 shows the thermoanalysis of form C.

FIG. 6 shows a thermoanalysis of form C

In the DSC diagram of form C a whole range of signals can be observed. The strongest signal is the melting point of the anhydrous form A at approx. 206° C., which is produced in the DSC experiment. Before the melting point a number of other endothermic and exothermic signals can be observed. Thus, for example, a very broad and weak endothermic signal can be seen between 30 and 100° C., which correlates with the main loss of weight in thermogravimetry (TR). A TG/IR coupling experiment provides the information that only water escapes from the sample in this temperature range.

An X-ray powder diagram taken of a sample maintained at a temperature of 100° C. shows different X-ray reflections from the starting material, suggesting that form C is a hydrate phase with stoichiometry somewhere in the region of a hemihydrate or monohydrate. The temperature-controlled sample is another anhydrous modification D, which only stable under anhydrous conditions. The D form melts at approx. 150° C. Another anhydrous crystal modification E crystallises from the melt, and when heated further melts at approx. 175° C. Finally, form A crystallises from the melt of form E. Form E is also a metastable crystal modification which occurs only at high temperatures.

The invention claimed is:

1. An anhydrous polymorph A of the compound 1-[(4-methyl-quinazolin-2-yl)methyl]-3-methyl-7-(2-butyn-1-yl)-8-(3-(R)-amino-piperidin-1-yl)-xanthine, characterised in that it melts at 206±3° C.

2. The polymorph A according to claim 1, characterised in that in the X-ray powder diagram it has characteristic reflections at the following d values: 11.59 A, 7.60 Å, 7.15 Å, 3.86 Å, 3.54 Å and 3.47 Å.

3. An anhydrous polymorph B of the compound 1-[(4-methyl-quinazolin-2-yl)methyl]-3-methyl-7-(2-butyn-1-yl)-8-(3-(R)-amino-piperidin-1-yl)-xanthine, characterised in that at a temperature of 10-40° C. it transforms reversibly into the polymorph A of claim 1.

4. The polymorph according to claim 3, characterised in that in the X-ray powder diagram it has alia characteristic reflections at the following d values: 11.3 Å, 9.36 Å, 7.48 Å, 7 Å and 3.77 Å.

5. An anhydrous polymorph E of the compound 1-[(4-methyl-quinazolin-2-yl)methyl]-3-methyl-7-(2-butyn-1-yl)-8-(3-(R)-amino-piperidin-1-yl)-xanthine, characterised in that it melts at 175±3° C.

6. A pharmaceutical composition comprising polymorph A according to claim 1, and one or more inert carriers or diluents.

7. A medicament containing 0.1% to 0.5% or 0.5% to 1.5% or 1% to 3% of polymorph A according to claim 1, in addition to one or more inert carriers.

8. A pharmaceutical composition comprising polymorph B according to claim 3, and one or more inert carriers or diluents.

9. A medicament containing 0.1% to 0.5% or 0.5% to 1.5% or 1% to 3% of polymorph B according to claim 3, in addition to one or more inert carriers.

10. The anhydrous polymorph A according to claim 1, characterized by its lattice metrics:

| Symmetry: | monoclinic |
|---|---|
| space group: | P |
| a: | 16.16(2) Å |
| b: | 17.02(1) Å |
| c: | 18.18(2) Å |
| ß: | 100.95(6)° |
| cell volume: | 4907(11) Å$^3$. |

11. The anhydrous polymorph A according to claim 2, wherein the reflection at 11.59 A in the X-ray powder diagram has a relative intensity of 100%.

12. The anhydrous polymorph A according to claim 11, wherein the X-ray powder diagram exhibits no reflections having a relative intensity of 1% or more at the following d values: 11.3 Å, 9.36 Å, 7.48 Å, and 7 Å.

13. The anhydrous polymorph B according to claim 3, characterised by its lattice metrics:

| Symmetry: | monoclinic |
|---|---|
| space group: | P2$_1$/c (# 14) |
| a: | 15.23(1) Å |
| b: | 16.94(1) Å |
| c: | 18.79(1) Å |
| ß: | 95.6(2)° |
| cell volume: | 4823(3) Å$^3$. |

14. The anhydrous polymorph B according to claim 4, wherein the reflection at 11.3 Å in the X-ray powder diagram has a relative intensity of 100%.

15. The anhydrous polymorph B according to claim 14, wherein the X-ray powder diagram exhibits no reflections having a relative intensity of 1% or more at the following d values: 11.59 Å, 7.60 Å, and 7.15 Å.

16. A pharmaceutical composition comprising polymorph A, as defined in claim 1 and one or more inert carriers.

17. A pharmaceutical composition comprising polymorph B, as defined in claim 3 and one or more inert carriers.

18. The medicament according to claim 7, containing 0.1% to 0.5% of the polymorph A.

19. The medicament according to claim 7, containing 0.5% to 1.5% of the polymorph A.

20. The medicament according to claim 7, containing 1% to 3% of the polymorph A.

21. The medicament according to claim 9, containing 0.1% to 0.5% of the polymorph B.

22. The medicament according to claim 9, containing 0.5% to 1.5% of the polymorph B.

23. The medicament according to claim 9, containing 1% to 3% of the polymorph B.

24. A pharmaceutical composition comprising polymorph A, as defined in claim 2 and one or more inert carriers.

25. A pharmaceutical composition comprising polymorph B, as defined in claim 4 and one or more inert carriers.

26. A medicament containing 0.1% to 0.5% or 0.5% to 1.5% or 1% to 3% of polymorph A as defined in claim 2, in addition to one or more inert carriers.

27. A medicament containing 0.1% to 0.5% or 0.5% to 1.5% or 1% to 3% of polymorph B as defined in claim in addition to one or more inert carriers.

28. The medicament according to claim 26, containing 0.1% to 0.5% of the polymorph A.

29. The medicament according to claim 26, containing 0.5% to 1.5% of the polymorph A.

30. The medicament according to claim 26, containing 1% to 3% of the polymorph A.

31. The medicament according to claim 27, containing 0.1% to 0.5% of the polymorph B.

32. The medicament according to claim 27, containing 0.5% to 1.5% of the polymorph B.

33. The medicament according to claim 27, containing 1% to 3% of the polymorph B.

34. The medicament according to claim 26, wherein the polymorph A has reflection at 11.59 A in the X-ray powder diagram having a relative intensity of 100%, and wherein the X-ray powder diagram exhibits no reflections having a relative intensity of 1% or more at the following d values: 11.3 Å, 9.36 Å, 7.48 Å, and 7 Å.

35. The medicament according to claim 27, wherein the polymorph B has reflection at 11.3 Å in the X-ray powder diagram having a relative intensity of 100%, and wherein the X-ray powder diagram exhibits no reflections having a relative intensity of 1% or more at the following d values: 11.59 Å, 7.60 Å, and 7.15 Å.

\* \* \* \* \*

UNITED STATES PATENT AND TRADEMARK OFFICE
CERTIFICATE OF CORRECTION

PATENT NO. : 11,084,819 B2  
APPLICATION NO. : 16/662406  
DATED : August 10, 2021  
INVENTOR(S) : Sieger et al.

Page 1 of 1

It is certified that error appears in the above-identified patent and that said Letters Patent is hereby corrected as shown below:

In the Claims

In Claim 27 at Column 8, Line 49, after the term "claim" add the term -- 4, --.

Signed and Sealed this  
Fifth Day of October, 2021

Drew Hirshfeld  
*Performing the Functions and Duties of the*  
*Under Secretary of Commerce for Intellectual Property and*  
*Director of the United States Patent and Trademark Office*